US006451790B1

(12) United States Patent
Gewehr et al.

(10) Patent No.: US 6,451,790 B1
(45) Date of Patent: Sep. 17, 2002

(54) AZADIOXACYCLOALKENES AND THEIR USE FOR COMBATING HARMFUL FUNGI AND ANIMAL PESTS

(75) Inventors: Markus Gewehr, Kastellaun; Hubert Sauter, Mannheim; Bernd Müller, Frankenthal; Wassilios Grammenos, Ludwigshafen; Andreas Gypser, Mannheim; Arne Ptock, Ludwigshafen; Oliver Cullmann, Mannheim; Jordi Tormo i Blasco, Limburgerhof; Eberhard Ammermann, Heppenheim; Siegfried Strathmann, Limburgerhof; Gisela Lorenz, Neustadt; Volker Harries, Frankenthal; Roland Götz, Neulussheim; Thomas Grote, Schifferstadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/889,164

(22) PCT Filed: Jan. 4, 2001

(86) PCT No.: PCT/EP00/00013

§ 371 (c)(1),
(2), (4) Date: Jul. 11, 2001

(87) PCT Pub. No.: WO00/42039

PCT Pub. Date: Jul. 20, 2000

(30) Foreign Application Priority Data

Jan. 13, 1999 (DE) .......................... 199 00 892

(51) Int. Cl.$^7$ .................... C07D 413/12; C07D 413/14; C07D 231/20; A01N 43/82; A01N 43/88
(52) U.S. Cl. ................. 514/229.2; 514/211.15; 514/360; 540/544; 544/65; 548/124; 548/263.8; 548/264.2; 548/366.1; 548/366.4; 548/368.7; 548/369.7
(58) Field of Search .......... 514/229.2, 211.15, 514/360; 544/65; 540/544; 548/124, 263.8, 264.2, 366.1, 366.4, 368.7, 369.7

(56) References Cited

FOREIGN PATENT DOCUMENTS

| DE | 29 33 985 | 4/1981 |
|---|---|---|
| EP | 178 826 | 4/1986 |
| EP | 253 213 | 1/1988 |
| EP | 378 755 | 7/1990 |
| EP | 757 042 | 2/1997 |
| EP | 846 691 | 6/1998 |
| JP | 09089653 | 4/1997 |
| WO | WO 94/19331 | 9/1994 |
| WO | WO 95/04728 | 2/1995 |
| WO | WO 95/29896 | 11/1995 |
| WO | WO 96/37480 | 11/1996 |
| WO | WO 97/00866 | 1/1997 |
| WO | WO 97/27189 | 7/1997 |
| WO | WO 97/46542 | 12/1997 |
| WO | WO 98/17653 | 4/1998 |
| WO | WO 98/25465 | 6/1998 |
| WO | WO 98/40351 | 9/1998 |
| WO | WO 98/40365 | 9/1998 |
| WO | WO 98/45289 | 10/1998 |

OTHER PUBLICATIONS

Organikum, vol. 14, (1986) p. 189.
Xu et al. "Unusual Reactivity of Pentafluorobenzyl Aromatic Ethers Under Friedel0Crafts Reaction Conditions" Tetrahedron Letters vol. 34, No. 24 (1993) pp. 3829–3832.
Greene "Protective Groups in Organic Synthesis" (1991) pp. 10–142.
Dai–Ho et al. "Exploratory, Mechanistic, and Synthetic Aspects of Silylarene–Iminium Salt SET Photochemistry, Studies of Diradical Cyclization Processes and Applications to Protoberberine Alakaloid Synthesis" J. Org. Chem. vol. 53 (1988) pp. 5113–5127.
Costello et al. "A Convenient Synthesis of Certain Hydroxymethyl Tetrahalogenobenzyl Bromides" Synthetic Communications vol. 17, No. 2, (1987) pp. 219–221.
Kornblum et al. "The Selective Replacements of the Aromatic Primary Amino Group by Hydrogen in Aromatic–Aliphatic Diamines" J. Amer. Chem. Soc. vol. 71 (1949) pp. 2137–2143.

(List continued on next page.)

Primary Examiner—Deepak R. Rao
(74) Attorney, Agent, or Firm—Keil & Weinkauf

(57) ABSTRACT

Compounds of formula I wherein
W is optionally substituted alkylene;
Y is N or $CR^a$;
$R^a$ is hydrogen, halogen or alkyl;
$R^1{}_n$ represents hydrogen or 1 to 4 substituents;
$R^2$ is hydrogen, nitro, cyano, halogen, alkyl, haloalkyl, alkoxy, alkylthio or alkoxycarbonyl;
$R^3$ is optionally substituted alkyl, cycloalkyl, aryl or hetaryl;
A is $N-OR^4$, $CH-OR^4$, $CH-SR^4$ or $CHR^5$;
$R^4$ is alkyl or haloalkyl;
$R^5$ is halogen, alkyl or haloalkyl;
methods and intermediates for their preparation. The compounds and compositions comprising them are useful for combating animal pests and harmful fungi.

9 Claims, No Drawings

OTHER PUBLICATIONS

Mease et al. "Intramolecular Nucleophilic Participation. V. The Role of the ortho Substituents in the Solovolysis of o–Nitrobenzhydryl Bromide and o–Nitrobenzyl Tosylate" J. Amer. Chem. Soc. vol. 90 (1968) pp. 1797–1801.

Madjdabadi et al. "A Simple Method for the Conversion of Adamantyl, Benzyl and Benzylhydryl Alcohols to their Corresponding Bromides and Chlorides and the Transhalogenation of Adamantyl, Benzyl, Benzylhydryl and Tertirafy Alkyl Bromides and Chlorides" Synthesis(1989) pp. 614–616.

AZADIOXACYCLOALKENES AND THEIR USE FOR COMBATING HARMFUL FUNGI AND ANIMAL PESTS

This application is a 371 of international application PCT/EP00/00013 filed Jan. 4, 2001 which international application was published in German.

The present invention relates to azadioxacycloalkenes of the formula I,

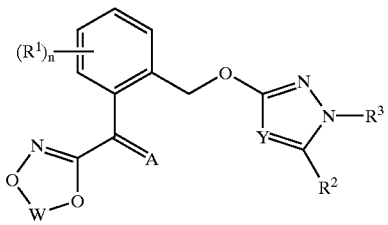

in which the substituents and the index have the following meanings:

Y is N or CR$^a$, where
  R$^a$ is hydrogen, halogen or $C_1$–$C_4$-alkyl;
n is 0, 1, 2, 3 or 4, where the substituents R$^1$ may be different if n is greater than 1;
R$^1$ is nitro, cyano, halogen, $C_1$–$C_6$-alkyl or,
  if n is greater than 1, additionally a bridge which is attached to two adjacent ring atoms and which contains three to four members selected from the group consisting of: 3 or 4 carbon atoms, 2 to 3 carbon atoms and 1 or 2 nitrogen, oxygen and/or sulfur atoms, where this bridge, together with the ring to which it is attached, may form a partially unsaturated or aromatic ring and where furthermore the carbon atoms of the bridge may be partially or fully substituted by halogen atoms or methyl groups;
R$^2$ is hydrogen, nitro, cyano, halogen, $C_1$–$C_4$-alkyl, $C_1$–$C_4$-haloalkyl, $C_1$–$C_4$-alkoxy, $C_1$–$C_4$-alkylthio or $C_1$–$C_4$-alkoxycarbonyl;
R$^3$ is $C_1$–$C_6$-alkyl which is unsubstituted or partially or fully halogenated or may carry one to three groups R$^b$,
  R$^b$ is halogen, cyano, nitro, hydroxyl, $C_1$–$C_6$-alkyl, $C_1$–$C_6$-haloalkyl, $C_1$–$C_6$-alkylcarbonyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkyl-amino, di-$C_1$–$C_6$-alkylamino, $C_2$–$C_6$-alkenyl, $C_2$–$C_6$-alkenyloxy, $C_3$–$C_6$-alkynyloxy and $C_1$–$C_4$-alkylenedioxy, which may be halogenated,
  $C_3$–$C_6$-cycloalkyl, aryl or hetaryl,
  where the cyclic systems may be partially or fully halogenated or may carry one to three groups R$^c$:
  R$^c$ is halogen, cyano, nitro, hydroxyl, mercapto, amino, carboxyl, aminocarbonyl, aminothiocarbonyl, alkyl, haloalkyl, alkenyl, alkenyloxy, alkynyloxy, alkoxy, haloalkoxy, alkylthio, alkylamino, dialkylamino, formyl, alkylcarbonyl, alkylsulfonyl, alkylsulfoxyl, alkoxycarbonyl, alkylcarbonyloxy, alkylaminocarbonyl, dialkylaminocarbonyl, alkylaminothiocarbonyl, dialkylaminothiocarbonyl, where the alkyl groups in these radicals contain 1 to 6 carbon atoms and the abovementioned alkenyl or alkynyl groups in these radicals contain 2 to 8 carbon atoms;
  is C(=NOR$^d$)-$\Gamma_1$-R$^d$, where R$^d$ is hydrogen or $C_1$–$C_6$-alkyl, $\Gamma$ is oxygen, sulfur or NR$^d$ and l is 0 or 1;
  and/or one to three of the following radicals: cycloalkyl, cycloalkoxy, heterocyclyl, heterocyclyloxy, where the cyclic systems contain 3 to 10 ring members; aryl, aryloxy, arylthio, aryl-$C_1$–$C_6$-alkoxy, aryl-$C_1$–$C_6$-alkyl, hetaryl, hetaryloxy, hetarylthio, where the aryl radicals preferably contain 6 to 10 ring members and the hetaryl radicals 5 or 6 ring members and where the cyclic systems may be partially or fully halogenated or may be substituted by one to three groups R$^b$;

A is =N—OR$^4$, =CH—OR$^4$ =CH—SR$^4$ or =CH—R$^5$, where
  R$^4$ is $C_1$–$C_4$-alkyl or $C_1$–$C_4$-haloalkyl,
  R$^5$ is halogen or a group R$^4$ and
W is $C_1$–$C_3$-alkylene which is unsubstituted or substituted by one or two groups R$^e$, where
  R$^e$ is halogen, cyano, $C_1$–$C_4$-alkyl, $C_1$–$C_4$-haloalkyl, $C_2$–$C_4$-alkenyl, $C_2$–$C_4$-haloalkenyl, $C_2$–$C_4$-alkynyl or $C_2$–$C_4$-haloalkynyl, $C_1$–$C_4$-alkoxy, $C_1$–$C_4$-haloalkoxy, $C_2$–$C_4$-alkenoxy, $C_2$–$C_4$-haloalkenyloxy, $C_2$–$C_4$-Alkynyloxy or $C_2$–$C_4$-haloalkynyloxy, $C_1$–$C_4$-alkylcarbonyloxy.

Moreover, the invention relates to processes for preparing these compounds, to compositions comprising them and to their use for controlling animal pests or harmful fungi.

EP-A 378 755, EP-A 757 042, WO-A 94/19331, WO-A 95/29896 and WO-A 96/37480 disclose 2-[pyrazolyl-4-oxymethylene]- and 2-[triazolyl-4-oxymethylene]phenyl acetic esters and corresponding amides for controlling animal pests and harmful fungi.

3-Phenylmethyleneazadioxacycloalkenes having substituents in the ortho position of the phenyl radical are disclosed in WO-A 95/04728, WO-A 97/27189, WO-A 98/17653, WO-A 98/25465, WO-A 98/40351, WO-A 98/40365, WO-A 98/45289, EP-A 846 691 and WO-A 97/00866.

It is an object of the present invention to provide compounds having improved activity.

We have found that this object is achieved by the compounds defined at the outset. Furthermore, we have found processes for their preparation, compositions comprising them and methods for controlling animal pests and harmful fungi using the compounds I.

The compounds of the formula I differ from the compounds known from the abovementioned publications WO-A 95/04728, WO-A 97/27189, WO-A 98/17653, WO-A 98/25465, WO-A 98/40351, WO-A 98/40365, WO-A 98/45289, EP-A 846 691 and WO-A 97/00866 in the methyleneoxy, pyrazolyl or triazolyl grouping and the phenyl ring and from the compounds known from EP-A 378 755, EP-A 757 042, WO-A 94/19331, WO-A 95/29896 and WO-A 96/37480 in the azadioxacycloalkene group. The compounds of the formula I have an activity against harmful fungi and animal pests which is higher than that of the known compounds.

The compounds of the formula I can be obtained analogously to the methods described in WO-A 95/04728, WO-A 97/46542 and WO-A 98/17653 or EP-A 378 755, EP-A 757 042, WO-A 94/19331 and WO-A 95/29896.

The compounds of the formula I can be obtained by diff different routes, and it is immaterial for the synthesis whether the group X where # denotes the link to the phenyl ring,

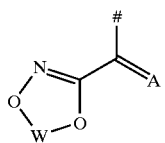

or the pyrazolyl or triazolyl grouping is synthesized first.

The compounds of the formula I are, for example, preferably obtained by reacting benzyl compounds of the formula II with hydroxypyrazols or the corresponding triazols of the formula III. In the formulae II and III, $R^1$, n, A, W, Y, $R^2$ and $R^3$ are as defined in formula I, in formula II, L is a nucleophilically replaceable group, for example halogen (e.g. chlorine or bromine) or an alkyl- or arylsulfonate (e.g. methylsulfonate, trifluoromethylsulfonate, phenylsulfonate and 4-methylphenylsulfonate).

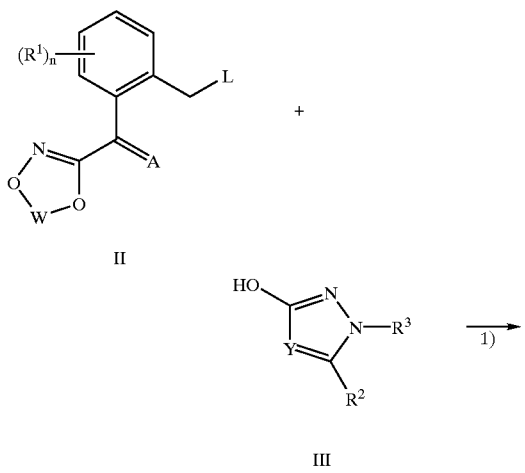

1) The etherification of the compounds II and III is usually carried out in an inert organic solvent at from 0° C. to 80° C., preferably at from 20° C. to 60° C., if appropriate in the presence of a base.

Suitable solvents are aromatic hydrocarbons, such as toluene, o-, m- and p-xylene, halogenated hydrocarbons, such as methylene chloride, chloroform and chlorobenzene, ethers, such as diethyl ether, diisopropyl ether, tert-butyl methyl ether, dioxane and tetrahydrofuran, nitriles, alcohols, ketones, such as acetone and methyl ethyl ketone, and also dimethyl sulfoxide, dimethylformamide, dimethylacetamide, 1,3-dimethylimidazolidin-2-one and 1,2-dimethyltetrahydro-2(1H)-pyrimidine, preferably methylene chloride, acetone, toluene, methyl tert-butyl ether and dimethylformamide. It is also possible to use mixtures of the solvents mentioned.

Suitable bases are, in general, inorganic compounds, such as alkali metal and alkaline earth metal hydroxides (e.g. lithium hydroxide, sodium hydroxide, potassium hydroxide and calcium hydroxide), alkali metal and alkaline earth metal oxides, alkali metal and alkaline earth metal hydrides, alkali metal amides, alkali metal and alkaline earth metal carbonates (e.g. lithium carbonate and calcium carbonate) and also alkali metal bicarbonates (e.g. sodium bicarbonate), organometallic compounds, in particular alkali metal alkyls, alkylmagnesium halides and also alkali metal and alkaline earth metal alkoxides (e.g. sodium methoxide, sodium ethoxide, potassium ethoxide, potassium tert-butoxide and dimethoxymagnesium), moreover organic bases, e.g. tertiary amines, such as trimethylamine, triethylamine, triisopropylethylamine [sic] and N-methylpiperidine, pyridine, substituted pyridines and also bicyclic amines. Particular preference is given to sodium hydroxide, potassium carbonate and potassium tert-butoxide. The bases are generally employed in equimolar amounts, in excess or, if appropriate, as solvents.

It may be advantageous for the reaction to add a catalytic amount of a crown ether (e.g. 18-crown-6 or 15-crown-5).

The reaction can also be carried out in two-phase systems comprising a solution of alkali metal or alkaline earth metal hydroxides or carbonates in water and in organic phase (e.g. aromatic and/or halogenated hydrocarbons). Suitable phase transfer catalysts are, for example, ammonium halides and ammonium tetrafluoroborates (e.g. benzyltriethylammonium chloride, benzyltributylammonium bromide, tetrabutyl ammonium chloride, hexadecyl trimethyl ammonium bromide or tetrabutylammonium tetrafluoroborate) and phosphonium halides (e.g. tetrabutylphosphonium chloride and tetraphenylphosphonium bromide).

It may be advantageous for the reaction to react initially the 3-hydroxypyrazol or -triazol with the base to give the corresponding hydroxylate, which is then reacted with the benzyl derivative.

Preference is given to using benzyl compounds II in which L is halogen.

The starting materials are generally reacted with one another in equimolar amounts. In terms of yield, it may be advantageous to employ an excess of hydroxypyrazol or -triazol, based on II.

The benzyl compounds II required for preparing the compounds I are known from the literature [cf. WO-A 95/04728; WO-A 98/17653]. They can be obtained, for example, by the following synthesis route:

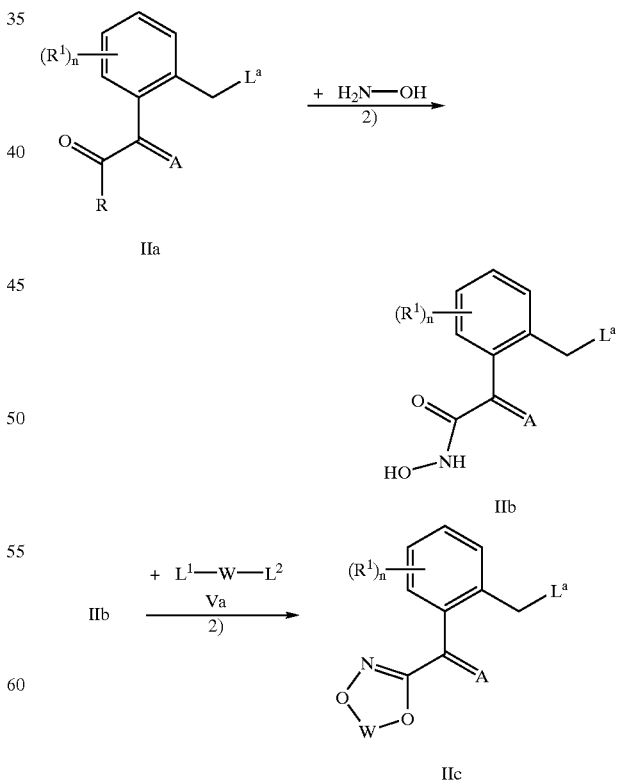

2) benzyl compounds of the formula IIa are reacted with hydroxylamine or its acid addition salt, if appropriate in the presence of a base or a dehydrating agent, such as N,N'-dicyclohexylcarbodiimide, or in the presence of a coupling reagent, such as, for example, 2-ethoxy-1-ethoxycarbonyl-1,2-dihydroquinoline (EEDQ), 1-isobutyloxycarbonyl-2-isobutyloxy-1,2-dihydroquinoline (IIDQ) or benzotriazol-1-yloxytris (dimethylamino)phosphonium hexafluorophosphate (BOP), to give the hydroxamic acids of the formula IIb which can be cyclized by reaction with compounds of the formula IVa to give IIc [cf. WO-A 95/04728].

In the formula IIa, $L^a$ is an oxygen atom which is protected by a protective group, R is halogen, alkylcarbonyloxy, OH, $C_1$–$C_4$-alkoxy or an activated ester, such as unsubstituted or substituted phenoxy (such as, for example, p-nitrophenoxy or pentafluorophenoxy), succinimidoxy or isourea. In the formula Va, W is as defined in claim 1 and $L^1$ and $L^2$ are each a nucleophilically replaceable group, such as halide, $C_1$–$C_4$-alkylsulfonate, $C_1$–$C_{12}$-alkylphenylsulfonate or mono-$C_1$–$C_4$-alkyl sulfate, or $L^1$ and $L^2$ together may denote a bridge-O-.

The reaction sequence IIa Γ IIb Γ IIc can be carried out in two steps or, preferably, in one step, i.e. without isolation of the hydroxamic acid IIb which is formed in the first process step. The process can be carried out analogously to the methods described in WO 95/04728, WO 97/00866 and EP-A 846 691.

Compounds of the formula Va are known from the literature, or they can be prepared by known methods [cf.: WO-A 95/04728; WO-A 97/00866; EP-A 846 691].

Benzyl compounds of the formula IIa are likewise known from the literature, or they can be prepared by known methods [cf.: EP-A 178 826; EP-A 253 213; WO-A 95/04728].

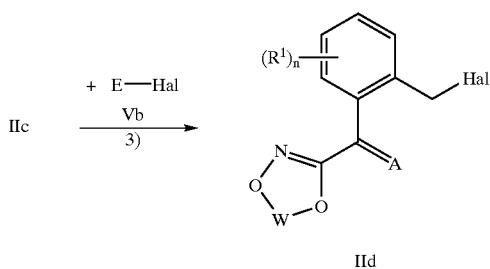

3) compounds II, in which L is halogen (formula IId), are obtained from compounds IIc by reaction with an acyl halide or a hydrohalic acid E-Hal (formula IVb), if appropriate in the presence of a Lewis acid [cf.: JP-A 90/89653; DE-A 29 33 985; WO-A 95/04728; Tetrahedron Lett., 34, (1993), 3829]. It may be advantageous to cleave off the protective group of the compound IIc beforehand in a separate step [cf. T. W. Greene, Protective Groups in Organic Chemistry, J. Wiley & Sons, 1991, pp. 10–142].

Alternatively, it is possible to initially cleave off the protective group from the compound IIc and to convert the resulting benzyl alcohol subsequently, by reaction with customary halogenating agents, such as, for example, $SOCl_2$, $BBr_3/SnCl_4$, $CCl_4$/triphenylphosphine or HBr, into the compound IId [cf.: Organikum, 16th edition 1988, p. 189ff., VEB Verlag der Wissenschaften, Berlin; Synthesis (1989) 614; J. Org. Chem., 53 (1988) 5113; Synth. Commun., 17 (1987) 219].

In the formula Vb, E is $C_1$–$C_4$-alkylcarbonyl, arylcarbonyl, $C_1$–$C_4$-alkylsulfonyl or arylsulfonyl and Hal is halogen (e.g. chlorine or bromine). Suitable compounds Vb are, in particular, carbonyl chlorides, such as, for example, acetyl chloride. A preferred Lewis acid is, for example, aluminum trichloride.

Compounds IId can also be obtained from o-tolyl compounds of the formula IIa, in which $L^a$ is hydrogen, by free-radical halogenation under generally customary conditions [cf. J. Amer. Chem. Soc., 71, (1949), 2137ff.; ibid., 90 (1968), 1797ff].

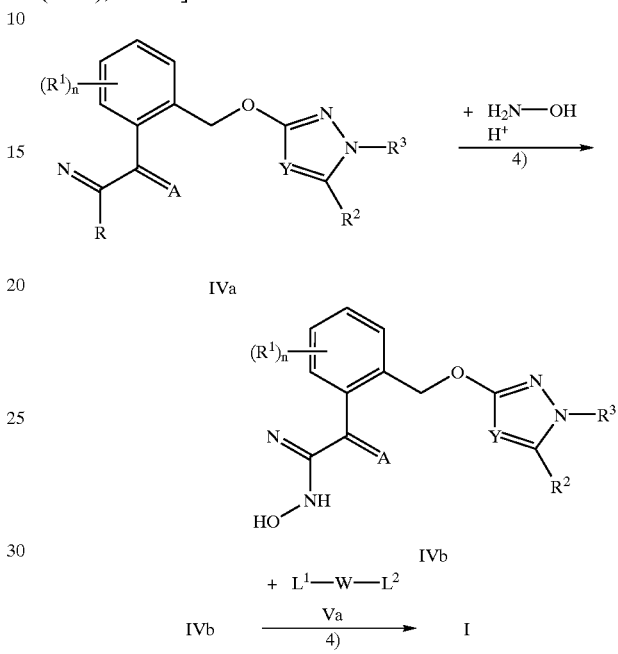

4) Alternatively, compounds of the formula I are also obtainable from compounds of the formula IVa. They can be converted into compounds of the formula I via the reaction sequence IVa Γ IVb Γ I, analogously to the conditions mentioned in section 2).

In the formula IVa, the substituent R is as defined for formula IIa and the other radicals are as defined for formula I.

The compounds IVa are known, and/or they are obtainable by known methods [cf.: EP-A 378 755, EP-A 757 042, WO-A 94/19331, WO-A 95/29896 and WO-A 96/37480].

The reaction mixtures are worked up in a customary manner, for example by mixing with water, phase separation and, if required, chromatographic purification of the crude products. Some of the intermediates and end products are obtained in the form of colorless or slightly brownish, viscous oils, which are purified or freed from volatile components under reduced pressure and at moderately elevated temperatures. If the intermediates and end products are obtained as solids, purification can also be carried out by recrystallization or digestion.

If individual compounds I are not obtainable by the routes described above, they can be prepared by derivatization of other compounds I.

Owing to their C═C— and C═N-double bonds, the preparation of the compounds I may yield E/Z isomer mixtures which can be separated into the individual compounds in a customary manner, for example by crystallization or chromatography.

However, if the synthesis yields isomer mixtures, a separation is generally not necessarily required since in some cases the individual isomers can be converted into one another during the preparation for use or upon use (for example under the action of light, acids or bases). Similar conversions may also occur after use, for example in the treatment of plants in the treated plant or in the harmful fungus or animal pest to be controlled.

In the symbol definitions given in the formulae above, collective terms were used which generally represent the following substituents:

halogen: fluorine, chlorine, bromine and iodine;

$C_1$–$C_4$-alkyl and the alkyl moieties of $C_1$–$C_4$-alkoxy, $C_1$–$C_4$-alkylthio, $C_1$–$C_4$-alkylamino, di-$C_1$–$C_4$-alkylamine or $C_1$–$C_4$-alkylcarbonyloxy: saturated, straight-chain or branched hydrocarbon radicals having 1 to 4 carbon atoms, specifically methyl, ethyl, propyl, 1-methylethyl, butyl, 1-methylpropyl, 2-methylpropyl, 1,1-dimethylethyl;

$C_1$–$C_6$-alkyl: saturated, straight-chain or branched hydrocarbon radicals having 1 to 6 carbon atoms, for example $C_1$–$C_4$-alkyl as mentioned above or pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

$C_1$–$C_3$-alkylene: methylene, ethylene or n-propylene;

$C_1$–$C_4$-haloalkyl and the haloalkyl moieties of $C_1$–$C_4$-haloalkoxy: straight-chain or branched alkyl groups having 1 to 4 carbon atoms (as mentioned above), where the hydrogen atoms in these groups may be partially or fully replaced by halogen atoms as mentioned above, for example $C_1$–$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

$C_3$–$C_4$-alkenyl: unsaturated, straight-chain or branched hydrocarbon radicals having 3 to 4 carbon atoms and a double bond in any position, for example 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl and 2-methyl-2-propenyl;

$C_2$–$C_4$-alkenyl and the alkenyl moieties of $C_2$–$C_4$-alkenyloxy: ethenyl or $C_3$–$C_4$-alkenyl (as mentioned above);

$C_2$–$C_4$-haloalkenyl and the haloalkenyl moieties of $C_2$–$C_4$-haloalkenyloxy: unsaturated, straight-chain or branched hydrocarbon radicals having 2 to 4 carbon atoms and a double bond in any position (as mentioned above), where the hydrogen atoms in these groups may be partially or fully replaced by halogen atoms as mentioned above, in particular by fluorine, chlorine and bromine;

$C_3$–$C_4$-alkynyl: straight-chain or branched hydrocarbon radicals having 3 to 4 carbon atoms and a triple bond in any position, for example ethynyl, 1-propynyl, 2-propynyl, 1-butynyl, 2-butynyl, 3-butynyl and 1-methyl-2-propynyl;

$C_2$–$C_4$-alkynyl and the alkynyl moieties of $C_2$–$C_4$-alkynyloxy: ethynyl or $C_3$–$C_4$-alkynyl (as mentioned above);

$C_3$–$C_4$-haloalkynyl and the haloalkynyl moieties of $C_2$–$C_4$-haloalkynyloxy: unsaturated, straight-chain or branched hydrocarbon radicals having 2 to 4 carbon atoms and a triple bond in any position (as mentioned above), where the hydrogen atoms in these groups may be partially or fully replaced by halogen atoms as mentioned above, in particular by fluorine, chlorine and bromine;

aryl: a mono- to tricyclic aromatic ring system containing 6 to 14 carbon ring members, for example phenyl, naphthyl and anthracenyl;

hetaryl: 5- or 6-membered heteroaromatics, for example 5-membered heteroaryl, containing one to four nitrogen atoms or one to three nitrogen atoms and one sulfur or oxygen atom: 5-membered heteroaryl groups which, in addition to carbon atoms, may contain one to four nitrogen atoms or one to three nitrogen atoms and one sulfur or oxygen atom as ring members, for example 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

benzo-fused 5-membered heteroaryl, containing one to three nitrogen atoms or one nitrogen atom and one oxygen or sulfur atom: 5-membered heteroaryl groups which, in addition to carbon atoms, may contain one to four nitrogen atoms or one to three nitrogen atoms and one sulfur or oxygen atom as ring members and in which two adjacent carbon ring members or one nitrogen and one adjacent carbon ring member may be bridged by a buta-1,3-dien-1,4-diyl group;

6-membered heteroaryl, containing one to four nitrogen atoms: 6-membered heteroaryl groups which, in addition to carbon atoms, may contain one to three or one to four nitrogen atoms as ring members, for example 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

With respect to the phenyl radical, the term "with or without substitution" is intended to express that this radical may be partially or fully halogenated [i.e. the hydrogen atoms of this radical may be partly or wholly replaced by identical or different halogen atoms as mentioned above (preferably fluorine, chlorine or bromine, in particular fluorine or chlorine)] and/or carry one to four (in particular one to three) of the following radicals:

halogen, cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylamino, di-$C_1$–$C_4$-alkylamino and $C_1$–$C_4$-alkylthio.

With respect to their intended use, preference is given to azadioxacycloalkenes of the formula I having the following substituents, where the preference is valid in each case on its own or in combination:

The particularly preferred embodiments of the intermediates with respect to the variables correspond to those of the radicals Y, n, A, W, $R^1$, $R^2$ and $R^3$ of formula I.

Particular preference is given to compounds I'.

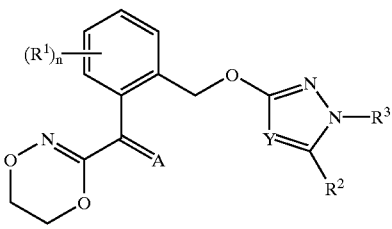

I'

Moreover, particular preference is given to compounds I in which A is =N—OCH$_3$, =CH—OCH$_3$ or =CH—CH$_3$.

Particular preference is given to compounds I in which A is =N—OR$^4$ or CH—R$^4$.

Furthermore, particular preference is given to compounds I in which A is =N—OCH$_3$ or =CH—CH$_3$.

Besides, particular preference is given to compounds I in which n is zero.

Likewise, particular preference is given to compounds I in which R$^1$ is 6-CH$_3$ or 6-Cl and n is 1.

Particular preference is also given to compounds I in which Y is N.

Moreover, particular preference is given to compounds I in which Y is CR$^a$.

Likewise, particular preference is given to compounds I in which R$^2$ is hydrogen.

Besides, particular preference is given to compounds I in which R$^3$ is C$_1$–C$_6$-alkyl which is unsubstituted or partially or fully halogenated or may carry one to three groups R$^b$.

Furthermore, particular preference is given to compounds I in which R$^3$ is phenyl or benzyl, where the phenyl ring may be partially or fully halogenated or may carry one to three groups R$^c$.

Moreover, particular preference is given to compounds I in which R$^3$ is pyridin-2-yl which may be partially or fully halogenated or may carry one to three groups R$^c$.

Particular preference is given to compounds IA in which Y is N, CH or C—CH$_3$, (R$^1$)$_n$ is hydrogen, 6-CH$_3$ or 6-Cl, R$^2$ is hydrogen or CH$_3$ and R$^3$ is cyclohexyl, benzyl, phenyl or 2-pyridyl, where the aromatic rings may be substituted by one or two halogen or trifluoromethyl groups.

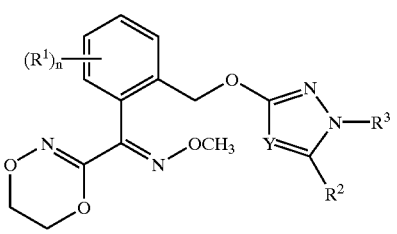

IA

Moreover, preference is given to compounds IB in which Y is N, CH or C—CH$_3$, (R$^1$)$_n$ is hydrogen, 6-CH$_3$ or 6-Cl, R$^2$ is hydrogen or CH$_3$ and R$^3$ is cyclohexyl, benzyl, phenyl or 2-pyridyl, where the aromatic rings may be substituted by one or two halogen or trifluoromethyl groups.

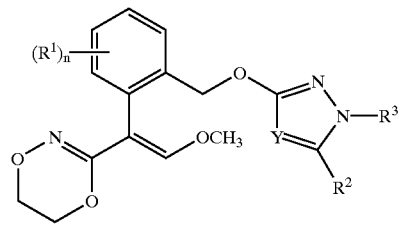

IB

Likewise, preference is given to compounds IC in which Y is N, CH or C—CH$_3$, (R$^1$)$_n$ is hydrogen, 6-CH$_3$ or 6-Cl, R$^2$ is hydrogen or CH$_3$ and R$^3$ is cyclohexyl, benzyl, phenyl or 2-pyridyl, where the aromatic rings may be substituted by one or two halogen or trifluoromethyl groups.

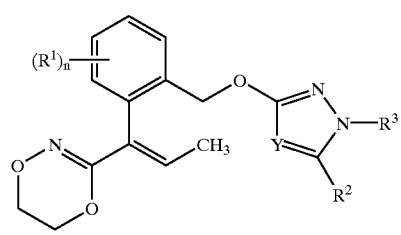

IC

Additionally, particular preference is given to compounds ID in which (R$^1$)$_n$ is hydrogen, 6-CH$_3$ or 6-Cl, Y is N, CH or C—CH$_3$, R$^2$ is hydrogen, CH$_3$ or chlorine, R$^c$ is halogen, nitro, cyano, C$_1$–C$_4$-alkyl, C$_1$–C$_6$-alkoxy, C$_1$–C$_2$-haloalkoxy, phenyl-C$_1$–C$_2$-alkoxy, C(CH$_3$)=NO—C$_1$–C$_3$-alkyl, cyclohexyl, phenyl or pyridyl and p is 0, 1 or 2.

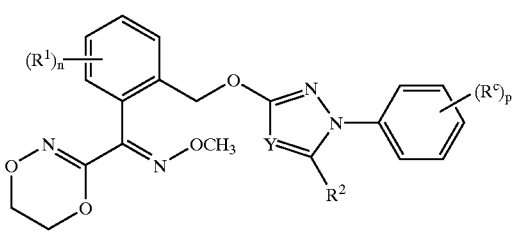

ID

Particular preference is also given to compounds IE in which (R$^1$)$_n$ is hydrogen, 6-CH$_3$ or 6-Cl, Y is N, CH or C—CH$_3$, R$^2$ is hydrogen, CH$_3$ or chlorine, R$^c$ is halogen, nitro, cyano, C$_1$–C$_4$-alkyl, C$_1$–C$_6$-alkoxy, C$_1$–C$_2$-haloalkoxy, phenyl-C$_1$–C$_2$-alkoxy, C(CH$_3$)=NO—C$_1$–C$_3$-alkyl, cyclohexyl, phenyl or pyridyl and p is 0, 1 or 2.

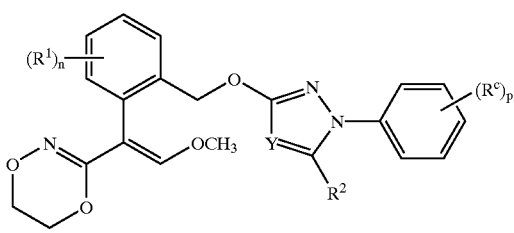

IE

Moreover, particular preference is given to compounds IF in which (R$^1$)$_n$ is hydrogen, 6-CH$_3$ or 6-Cl, Y is N, CH or C—CH$_3$, R$^2$ is hydrogen, CH$_3$ or chlorine, R$^c$ is halogen, nitro, cyano, C$_1$–C$_4$-alkyl, C$_1$–C$_6$-alkoxy, C$_1$–C$_2$- haloalkoxy, phenyl-$C_1$-$C_2$-alkoxy, $C(CH_3)$=NO—$C_1$-$C_3$-alkyl, cyclohexyl, phenyl or pyridyl and p is 0, 1 or 2.

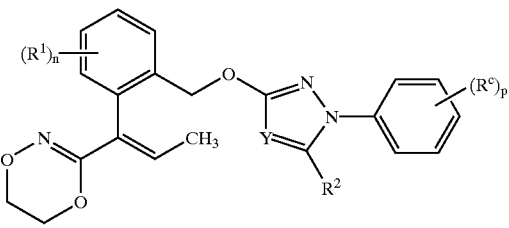

IF

Likewise, particular preference is given to compounds IG, in which $(R^1)_n$ is hydrogen, 6-$CH_3$ or 6-Cl, Y is N, CH or C—$CH_3$, $R^2$ is hydrogen, $CH_3$ or chlorine, $R^c$ is halogen, methyl, trifluoromethyl, methoxy or trifluoromethoxy and p is 0 or 1.

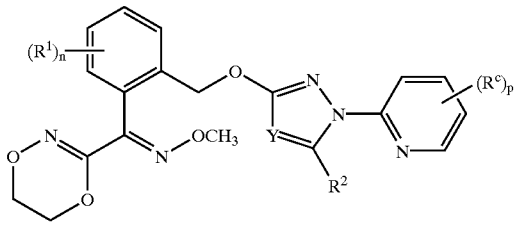

IG

Additionally, particular preference is given to compounds IH in which $(R^1)_n$ is hydrogen, 6-$CH_3$ or 6-Cl, Y is N, CH or C—$CH_3$, $R^2$ is hydrogen, $CH_3$ or chlorine, $R^c$ is halogen, methyl, trifluoromethyl, methoxy or trifluoromethoxy and p is 0 or 1.

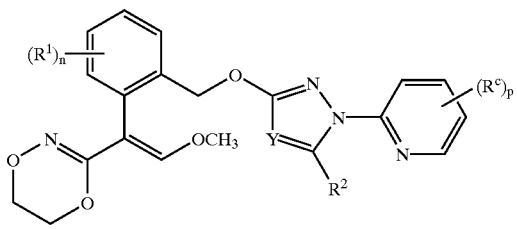

IH

Furthermore, particular preference is given to compounds IJ in which $(R^1)_n$ is hydrogen, 6-$CH_3$ or 6-Cl, Y is N, CH or C—$CH_3$, $R^2$ is hydrogen, $CH_3$ or chlorine, $R^c$ is halogen, methyl, trifluoromethyl, methoxy or trifluoromethoxy and p is 0 or 1.

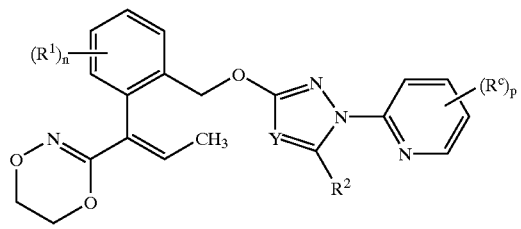

IJ

With respect to their use, particular preference is given to the compounds I compiled in the tables below. The groups mentioned in the tables for a substituent are furthermore for their part, independently of the combination in which they are mentioned, a particularly preferred embodiment of the respective substituents.

Table 1
Compounds of the formula IA, in which Y is N and $(R^1)_n$, $R^2$ and $R^3$ correspond to one row in Table A
Table 2
Compounds of the formula IA, in which Y is CH and $(R^1)_n$, $R^2$ and $R^3$ correspond to one row in Table A
Table 3
Compounds of the formula IA, in which Y is C—$CH_3$ and $(R^1)_n$, $R^2$ and $R^3$ correspond to one row in Table A
Table 4
Compounds of the formula IA, in which Y is C—Cl and $(R^1)_n$, $R^2$ and $R^3$ correspond to one row in Table A
Table 5
Compounds of the formula IB, in which Y is N and $(R^1)_n$, $R^2$ and $R^3$ correspond to one row in Table A
Table 6
Compounds of the formula IB, in which Y is CH and $(R^1)_n$, $R^2$ and $R^3$ correspond to one row in Table A
Table 7
Compounds of the formula IB, in which Y is C—$CH_3$ and $(R^1)_n$, $R^2$ and $R^3$ correspond to one row in Table A
Table 8
Compounds of the formula IB, in which Y is C—Cl and $(R^1)_n$, $R^2$ and $R^3$ correspond to one row in Table A
Table 9
Compounds of the formula IC, in which Y is N and $(R^1)_n$, $R^2$ and $R^3$ correspond to one row in Table A
Table 10
Compounds of the formula IC, in which Y is CH and $(R^1)_n$, $R^2$ and $R^3$ correspond to one row in Table A
Table 11
Compounds of the formula IC, in which Y is C—$CH_3$ and $(R^1)_n$, $R^2$ and $R^3$ correspond to one row in Table A
Table 12
Compounds of the formula IC, in which Y is C—Cl and $(R^1)_n$, $R^2$ and $R^3$ correspond to one row in Table A
Table 13
Compounds of the formula ID, in which $(R^1)_n$ is hydrogen, Y is N and $R^2$ is hydrogen and $(R^c)_p$ correspond to one row in Table B
Table 14
Compounds of the formula ID, in which $(R^1)_n$ is hydrogen, Y is CH and $R^2$ is hydrogen and $(R^c)_p$ correspond to one row in Table B
Table 15
Compounds of the formula ID, in which $(R^1)_n$ is hydrogen, Y is C—$CH_3$ and $R^2$ is hydrogen and $(R^c)_p$ correspond to one row in Table B
Table 16
Compounds of the formula ID, in which $(R^1)_n$ is hydrogen, Y is C—Cl and $R^2$ is hydrogen and $(R^c)_p$ correspond to one row in Table B
Table 17
Compounds of the formula ID, in which $(R^1)_n$ is 6-chloro, Y is N and $R^2$ is hydrogen and $(R^c)_p$ correspond to one row in Table B
Table 18
Compounds of the formula ID, in which $(R^1)_n$ is 6-chloro, Y is CH and $R^2$ is hydrogen and $(R^c)_p$ correspond to one row in Table B
Table 19
Compounds of the formula ID, in which $(R^1)_n$ is 6-chloro, Y is C—$CH_3$ and $R^2$ is hydrogen and $(R^c)_p$ correspond to one row in Table B Table 20
Compounds of the formula ID, in which $(R^1)_n$ is 6-chloro, Y is C—Cl and $R^2$ is hydrogen and $(R^c)_p$ correspond to one row in Table B Table 21
Compounds of the formula ID, in which $(R^1)_n$ is 6-methyl, Y is N and $R^2$ is hydrogen and $(R^c)_p$ correspond to one row in Table B Table 22
Compounds of the formula ID, in which $(R^1)_n$ is 6-methyl, Y is CH and $R^2$ is hydrogen and $(R^c)_p$ correspond to one row in Table B Table 23
Compounds of the formula ID, in which $(R^1)_n$ is 6-methyl, Y is C—$CH_3$ and $R^2$ is hydrogen and $(R^c)_p$ correspond to one row in Table B Table 24
Compounds of the formula ID, in which $(R^1)_n$ is 6-methyl, Y is C—Cl and $R^2$ is hydrogen and $(R^c)_p$ correspond to one row in Table B Table 25
Compounds of the formula ID, in which $(R^1)_n$ is hydrogen, Y is N and $R^2$ is methyl and $(R^c)_p$ correspond to one row in Table B Table 26
Compounds of the formula ID, in which $(R^1)_n$ is hydrogen, Y is CH and $R^2$ is methyl and $(R^c)_p$ correspond to one row in Table B Table 27
Compounds of the formula ID, in which $(R^1)_n$ is hydrogen, Y is C—$CH_3$ and $R^2$ is methyl and $(R^c)_p$ correspond to one row in Table B Table 28
Compounds of the formula ID, in which $(R^1)_n$ is hydrogen, Y is C—Cl and $R^2$ is methyl and $(R^c)_p$ correspond to one row in Table B Table 29
Compounds of the formula ID, in which $(R^1)_n$ is 6-chloro, Y is N and $R^2$ is methyl and $(R^c)_p$ correspond to one row in Table B Table 30
Compounds of the formula ID, in which $(R^1)_n$ is 6-chloro, Y is CH and $R^2$ is methyl and $(R^c)_p$ correspond to one row in Table B Table 31
Compounds of the formula ID, in which $(R^1)_n$ is 6-chloro, Y is C—$CH_3$ and $R^2$ is methyl and $(R^c)_p$ correspond to one row in Table B Table 32
Compounds of the formula ID, in which $(R^1)_n$ is 6-chloro, Y is C—Cl and $R^2$ is methyl and $(R^c)_p$ correspond to one row in Table B Table 33
Compounds of the formula ID, in which $(R^1)_n$ is 6-methyl, Y is N and $R^2$ is methyl and $(R^c)_p$ correspond to one row in Table B Table 34
Compounds of the formula ID, in which $(R^1)_n$ is 6-methyl, Y is CH and $R^2$ is methyl and $(R^c)_p$ correspond to one row in Table B Table 35
Compounds of the formula ID, in which $(R^1)_n$ is 6-methyl, Y is C—$CH_3$ and $R^2$ is methyl and $(R^c)_p$ correspond to one row in Table B Table 36
Compounds of the formula ID, in which $(R^1)_n$ is 6-methyl, Y is C—Cl and $R^2$ is methyl and $(R^c)_p$ correspond to one row in Table B Table 37
Compounds of the formula ID, in which $(R^1)_n$ is hydrogen, Y is N and $R^2$ is trifluoromethyl and $(R^c)_p$ correspond to one row in Table B Table 38
Compounds of the formula ID, in which $(R^1)_n$ is hydrogen, Y is CH and $R^2$ is trifluoromethyl and $(R^c)_p$ correspond to one row in Table B Table 39
Compounds of the formula ID, in which $(R^1)_n$ is hydrogen, Y is C—$CH_3$ and $R^2$ is trifluoromethyl and $(R^c)_p$ correspond to one row in Table B Table 40
Compounds of the formula ID, in which $(R^1)_n$ is hydrogen, Y is C—Cl and $R^2$ is trifluoromethyl and $(R^c)_p$ correspond to one row in Table B Table 41
Compounds of the formula ID, in which $(R^1)_n$ is 6-chloro, Y is N and $R^2$ is trifluoromethyl and $(R^c)_p$ correspond to one row in Table B Table 42
Compounds of the formula ID, in which $(R^1)_n$ is 6-chloro, Y is CH and $R^2$ is trifluoromethyl and $(R^c)_p$ correspond to one row in Table B Table 43
Compounds of the formula ID, in which $(R^1)_n$ is 6-chloro, Y is C—$CH_3$ and $R^2$ is trifluoromethyl and $(R^c)_p$ correspond to one row in Table B Table 44
Compounds of the formula ID, in which $(R^1)_n$ is 6-chloro, Y is C—Cl and $R^2$ is trifluoromethyl and $(R^c)_p$ correspond to one row in Table B Table 45
Compounds of the formula ID, in which $(R^1)_n$ is 6-methyl, Y is N and $R^2$ is trifluoromethyl and $(R^c)_p$ correspond to one row in Table B Table 46
Compounds of the formula ID, in which $(R^1)_n$ is 6-methyl, Y is CH and $R^2$ is trifluoromethyl and $(R^c)_p$ correspond to one row in Table B Table 47
Compounds of the formula ID, in which $(R^1)_n$ is 6-methyl, Y is C—$CH_3$ and $R^2$ is trifluoromethyl and $(R^c)_p$ correspond to one row in Table B Table 48
Compounds of the formula ID, in which $(R^1)_n$ is 6-methyl, Y is C—Cl and $R^2$ is trifluoromethyl and $(R^c)_p$ correspond to one row in Table B Table 49
Compounds of the formula IE, in which $(R^1)_n$ is hydrogen, Y is N and $R^2$ is hydrogen and $(R^c)_p$ correspond to one row in Table B Table 50
Compounds of the formula IE, in which $(R^1)_n$ is hydrogen, Y is CH and $R^2$ is hydrogen and $(R^c)_p$ correspond to one row in Table B Table 51
Compounds of the formula IE, in which $(R^1)_n$ is hydrogen, Y is C—$CH_3$ and $R^2$ is hydrogen and $(R^c)_p$ correspond to one row in Table B Table 52
Compounds of the formula IE, in which $(R^1)_n$ is hydrogen, Y is C—Cl and $R^2$ is hydrogen and $(R^c)_p$ correspond to one row in Table B Table 53
Compounds of the formula IE, in which $(R^1)_n$ is 6-chloro, Y is N and $R^2$ is hydrogen and $(R^c)_p$ correspond to one row in Table B Table 54
Compounds of the formula IE, in which $(R^1)_n$ is 6-chloro, Y is CH and $R^2$ is hydrogen and $(R^c)_p$ correspond to one row in Table B Table 55
Compounds of the formula IE, in which $(R^1)_n$ is 6-chloro, Y is C—$CH_3$ and $R^2$ is hydrogen and $(R^c)_p$ correspond to one row in Table B Table 56
Compounds of the formula IE, in which $(R^1)_n$ is 6-chloro, Y is C—Cl and $R^2$ is hydrogen and $(R^c)_p$ correspond to one row in Table B Table 57
Compounds of the formula IE, in which $(R^1)_n$ is 6-methyl, Y is N and $R^2$ is hydrogen and $(R^c)_p$ correspond to one row in Table B Table 58
Compounds of the formula IE, in which $(R^1)_n$ is 6-methyl, Y is CH and $R^2$ is hydrogen and $(R^c)_p$ correspond to one row in Table B Table 59
Compounds of the formula IE, in which $(R^1)_n$ is 6-methyl, Y is C—$CH_3$ and $R^2$ is hydrogen and $(R^c)_p$ correspond to one row in Table B Table 60
Compounds of the formula IE, in which $(R^1)_n$ is 6-methyl, Y is C—Cl and $R^2$ is hydrogen and $(R^c)_p$ correspond to one row in Table B Table 61
Compounds of the formula IE, in which $(R^1)_n$ is hydrogen, Y is N and $R^2$ is methyl and $(R^c)_p$ correspond to one row in Table B Table 62
Compounds of the formula IE, in which $(R^1)_n$ is hydrogen, Y is CH and $R^2$ is methyl and $(R^c)_p$ correspond to one row in Table B Table 63
Compounds of the formula IE, in which $(R^1)_n$ is hydrogen, Y is C—$CH_3$ and $R^2$ is methyl and $(R^c)_p$ correspond to one row in Table B Table 64
Compounds of the formula IE, in which $(R^1)_n$ is hydrogen, Y is C—Cl and $R^2$ is methyl and $(R^c)_p$ correspond to one row in Table B Table 65
Compounds of the formula IE, in which $(R^1)_n$ is 6-chloro, Y is N and $R^2$ is methyl and $(R^c)_p$ correspond to one row in Table B Table 66
Compounds of the formula IE, in which $(R^1)_n$ is 6-chloro, Y is CH and $R^2$ is methyl and $(R^c)_p$ correspond to one row in Table B Table 67
Compounds of the formula IE, in which $(R^1)_n$ is 6-chloro, Y is C—$CH_3$ and $R^2$ is methyl and $(R^c)_p$ correspond to one row in Table B Table 68
Compounds of the formula IE, in which $(R^1)_n$ is 6-chloro, Y is C—Cl and $R^2$ is methyl and $(R^c)_p$ correspond to one row in Table B Table 69
Compounds of the formula IE, in which $(R^1)_n$ is 6-methyl, Y is N and $R^2$ is methyl and $(R^c)_p$ correspond to one row in Table B Table 70
Compounds of the formula IE, in which $(R^1)_n$ is 6-methyl, Y is CH and $R^2$ is methyl and $(R^c)_p$ correspond to one row in Table B Table 71
Compounds of the formula IE, in which $(R^1)_n$ is 6-methyl, Y is C—$CH_3$ and $R^2$ is methyl and $(R^c)_p$ correspond to one row in Table B Table 72
Compounds of the formula IE, in which $(R^1)_n$ is 6-methyl, Y is C—Cl and $R^2$ is methyl and $(R^c)_p$ correspond to one row in Table B Table 73
Compounds of the formula IE, in which $(R^1)_n$ is hydrogen, Y is N and $R^2$ is trifluoromethyl and $(R^c)_p$ correspond to one row in Table B Table 74
Compounds of the formula IE, in which $(R^1)_n$ is hydrogen, Y is CH and $R^2$ is trifluoromethyl and $(R^c)_p$ correspond to one row in Table B Table 75
Compounds of the formula IE, in which $(R^1)_n$ is hydrogen, Y is C—$CH_3$ and $R^2$ is trifluoromethyl and $(R^c)_p$ correspond to one row in Table B Table 76
Compounds of the formula IE, in which $(R^1)_n$ is hydrogen, Y is C—Cl and $R^2$ is trifluoromethyl and $(R^c)_p$ correspond to one row in Table B Table 77
Compounds of the formula IE, in which $(R^1)_n$ is 6-chloro, Y is N and $R^2$ is trifluoromethyl and $(R^c)_p$ correspond to one row in Table B Table 78
Compounds of the formula IE, in which $(R^1)_n$ is 6-chloro, Y is CH and $R^2$ is trifluoromethyl and $(R^c)_p$ correspond to one row in Table B Table 79
Compounds of the formula IE, in which $(R^1)_n$ is 6-chloro, Y is C—$CH_3$ and $R^2$ is trifluoromethyl and $(R^c)_p$ correspond to one row in Table B Table 80
Compounds of the formula IE, in which $(R^1)_n$ is 6-chloro, Y is C—Cl and $R^2$ is trifluoromethyl and $(R^c)_p$ correspond to one row in Table B Table 81
Compounds of the formula IE, in which $(R^1)_n$ is 6-methyl, Y is N and R is trifluoromethyl and $(R^c)_p$ correspond to one row in Table B Table 82
Compounds of the formula IE, in which $(R^1)_n$ is 6-methyl, Y is CH and $R^2$ is trifluoromethyl and $(R^c)_p$ correspond to one row in Table B Table 83
Compounds of the formula IE, in which $(R^1)_n$ is 6-methyl, Y is C—$CH_3$ and $R^2$ is trifluoromethyl and $(R^c)_p$ correspond to one row in Table B Table 84
Compounds of the formula IE, in which $(R^1)_n$ is 6-methyl, Y is C—Cl and $R^2$ is trifluoromethyl and $(R^c)_p$ correspond to one row in Table B Table 85
Compounds of the formula IF, in which $(R^1)_n$ is hydrogen, Y is N and $R^2$ is hydrogen and $(R^c)_p$ correspond to one row in Table B Table 86
Compounds of the formula IF, in which $(R^1)_n$ is hydrogen, Y is CH and $R^2$ is hydrogen and $(R^c)_p$ correspond to one row in Table B Table 87
Compounds of the formula IF, in which $(R^1)_n$ is hydrogen, Y is C—$CH_3$ and $R^2$ is hydrogen and $(R^c)_p$ correspond to one row in Table B Table 88
Compounds of the formula IF, in which $(R^1)_n$ is hydrogen, Y is C—Cl and $R^2$ is hydrogen and $(R^c)_p$ correspond to one row in Table B Table 89
Compounds of the formula IF, in which $(R^1)_n$ is 6-chloro, Y is N and $R^2$ is hydrogen and $(R^c)_p$ correspond to one row in Table B Table 90
Compounds of the formula IF, in which $(R^1)_n$ is 6-chloro, Y is CH and $R^2$ is hydrogen and $(R^c)_p$ correspond to one row in Table B Table 91
Compounds of the formula IF, in which $(R^1)_n$ is 6-chloro, Y is C—CH$_3$ and $R^2$ is hydrogen and $(R^c)_p$ correspond to one row in Table B Table 92
Compounds of the formula IF, in which $(R^1)_n$ is 6-chloro, Y is C—Cl and $R^2$ is hydrogen and $(R^c)_p$, correspond to one row in Table B Table 93
Compounds of the formula IF, in which $(R^1)_n$ is 6-methyl, Y is N and $R^2$ is hydrogen and $(R^c)_p$ correspond to one row in Table B Table 94
Compounds of the formula IF, in which $(R^1)_n$ is 6-methyl, Y is CH and $R^2$ is hydrogen and $(R^c)_p$ correspond to one row in Table B Table 95
Compounds of the formula IF, in which $(R^1)_n$ is 6-methyl, Y is C—CH$_3$ and $R^2$ is hydrogen and $(R^c)_p$ correspond to one row in Table B Table 96
Compounds of the formula IF, in which $(R^1)_n$ is 6-methyl, Y is C—Cl and $R^2$ is hydrogen and $(R^c)_p$ correspond to one row in Table B Table 97
Compounds of the formula IF, in which $(R^1)_n$ is hydrogen, Y is N and $R^2$ is methyl and $(R^c)_p$ correspond to one row in Table B Table 98
Compounds of the formula IF, in which $(R^1)_n$ is hydrogen, Y is CH and $R^2$ is methyl and $(R^c)_p$ correspond to one row in Table B Table 99
Compounds of the formula IF, in which $(R^1)_n$ is hydrogen, Y is C—CH$_3$ and $R^2$ is methyl and $(R^c)_p$ correspond to one row in Table B Table 100
Compounds of the formula IF, in which $(R^1)_n$ is hydrogen, Y is C—Cl and $R^2$ is methyl and $(R^c)_p$ correspond to one row in Table B Table 101
Compounds of the formula IF, in which $(R^1)_n$ is 6-chloro, Y is N and $R^2$ is methyl and $(R^c)_p$ correspond to one row in Table B Table 102
Compounds of the formula IF, in which $(R^1)_n$ is 6-chloro, Y is CH and $R^2$ is methyl and $(R^c)_p$ correspond to one row in Table B Table 103
Compounds of the formula IF, in which $(R^1)_n$ is 6-chloro, Y is C—CH$_3$ and $R^2$ is methyl and $(R^c)_p$ correspond to one row in Table B Table 104
Compounds of the formula IF, in which $(R^1)_n$ is 6-chloro, Y is C—Cl and $R^2$ is methyl and $(R^c)_p$ correspond to one row in Table B Table 105
Compounds of the formula IF, in which $(R^1)_n$ is 6-methyl, Y is N and $R^2$ is methyl and $(R^c)_p$, correspond to one row in Table B Table 106
Compounds of the formula IF, in which $(R^1)_n$ is 6-methyl, Y is CH and $R^2$ is methyl and $(R^c)_p$ correspond to one row in Table B Table 107
Compounds of the formula IF, in which $(R^1)_n$ is 6-methyl, Y is C—CH$_3$ and $R^2$ is methyl and $(R^c)_p$ correspond to one row in Table B Table 108
Compounds of the formula IF, in which $(R^1)_n$ is 6-methyl, Y is C—Cl and $R^2$ is methyl and $(R^c)_p$ correspond to one row in Table B Table 109
Compounds of the formula IF, in which $(R^1)_n$ is hydrogen, Y is N and $R^2$ is trifluoromethyl and $(R^c)_p$ correspond to one row in Table B Table 110
Compounds of the formula IF, in which $(R^1)_n$ is hydrogen, Y is CH and $R^2$ is trifluoromethyl and $(R^c)_p$ correspond to one row in Table B Table 111
Compounds of the formula IF, in which $(R^1)_n$ is hydrogen, Y is C—CH$_3$ and $R^2$ is trifluoromethyl and $(R^c)_p$ correspond to one row in Table B Table 112
Compounds of the formula IF, in which $(R^1)_n$ is hydrogen, Y is C—Cl and $R^2$ is trifluoromethyl and $(R^c)_p$ correspond to one row in Table B Table 113
Compounds of the formula IF, in which $(R^1)_n$ is 6-chloro, Y is N and $R^2$ is trifluoromethyl and $(R^c)_p$ correspond to one row in Table B Table 114
Compounds of the formula IF, in which $(R^1)_n$ is 6-chloro, Y is CH and $R^2$ is trifluoromethyl and $(R^c)_p$ correspond to one row in Table B Table 115
Compounds of the formula IF, in which $(R^1)_n$ is 6-chloro, Y is C—CH$_3$ and $R^2$ is trifluoromethyl and $(R^c)_p$ correspond to one row in Table B Table 116
Compounds of the formula IF, in which $(R^1)_n$ is 6-chloro, Y is C—Cl and $R^2$ is trifluoromethyl and $(R^c)_p$ correspond to one row in Table B Table 117
Compounds of the formula IF, in which $(R^1)_n$ is 6-methyl, Y is N and $R^2$ is trifluoromethyl and $(R^c)_p$ correspond to one row in Table B Table 118
Compounds of the formula IF, in which $(R^1)_n$ is 6-methyl, Y is CH and $R^2$ is trifluoromethyl and $(R^c)_p$ correspond to one row in Table B Table 119
Compounds of the formula IF, in which $(R^1)_n$ is 6-methyl, Y is C—CH$_3$ and $R^2$ is trifluoromethyl and $(R^c)_p$ correspond to one row in Table B Table 120
Compounds of the formula IF, in which $(R^1)_n$ is 6-methyl, Y is C—Cl and $R^2$ is trifluoromethyl and $(R^c)_p$ correspond to one row in Table B Table 121
Compounds of the formula IG, in which $(R^1)_n$ is hydrogen, Y is N and $R^2$ is hydrogen and $(R^c)_p$ correspond to one row in Table C Table 122
Compounds of the formula IG, in which $(R^1)_n$ is hydrogen, Y is CH and $R^2$ is hydrogen and $(R^c)_p$ correspond to one row in Table C Table 123
Compounds of the formula IG, in which $(R^1)_n$ is hydrogen, Y is C—$CH_3$ and $R^2$ is hydrogen and $(R^c)_p$ correspond to one row in Table C Table 124
Compounds of the formula IG, in which $(R^1)_n$ is hydrogen, Y is C—Cl and $R^2$ is hydrogen and $(R^c)_p$ correspond to one row in Table C Table 125
Compounds of the formula IG, in which $(R^1)_n$ is 6-chloro, Y is N and $R^2$ is hydrogen and $(R^c)_p$ correspond to one row in Table C Table 126
Compounds of the formula IG, in which $(R^1)_n$ is 6-chloro, Y is CH and $R^2$ is hydrogen and $(R^c)_p$ correspond to one row in Table C Table 127
Compounds of the formula IG, in which $(R^1)_n$ is 6-chloro, Y is C—$CH_3$ and $R^2$ is hydrogen and $(R^c)_p$ correspond to one row in Table C Table 128
Compounds of the formula IG, in which $(R^1)_n$ is 6-chloro, Y is C—Cl and $R^2$ is hydrogen and $(R^c)_p$ correspond to one row in Table C Table 129
Compounds of the formula IG, in which $(R^1)_n$ is 6-methyl, Y is N and $R^2$ is hydrogen and $(R^c)_p$ correspond to one row in Table C Table 130
Compounds of the formula IG, in which $(R^1)_n$ is 6-methyl, Y is CH and $R^2$ is hydrogen and $(R^c)_p$ correspond to one row in Table C Table 131
Compounds of the formula IG, in which $(R^1)_n$ is 6-methyl, Y is C—$CH_3$ and $R^2$ is hydrogen and $(R^c)_p$ correspond to one row in Table C Table 132
Compounds of the formula IG, in which $(R^1)_n$ is 6-methyl, Y is C—Cl and $R^2$ is hydrogen and $(R^c)_p$ correspond to one row in Table C Table 133
Compounds of the formula IG, in which $(R^1)_n$ is hydrogen, Y is N and $R^2$ is methyl and $(R^c)_p$ correspond to one row in Table C Table 134
Compounds of the formula IG, in which $(R^1)_n$ is hydrogen, Y is CH and $R^2$ is methyl and $(R^c)_p$ correspond to one row in Table C Table 135
Compounds of the formula IG, in which $(R^1)_n$ is hydrogen, Y is C—$CH_3$ and $R^2$ is methyl and $(R^c)_p$ correspond to one row in Table C Table 136
Compounds of the formula IG, in which $(R^1)_n$ is hydrogen, Y is C—Cl and $R^2$ is methyl and $(R^c)_p$ correspond to one row in Table C Table 137
Compounds of the formula IG, in which $(R^1)_n$ is 6-chloro, Y is N and $R^2$ is methyl and $(R^c)_p$ correspond to one row in Table C Table 138
Compounds of the formula IG, in which $(R^1)_n$ is 6-chloro, Y is CH and $R^2$ is methyl and $(R^c)_p$ correspond to one row in Table C Table 139
Compounds of the formula IG, in which $(R^1)_n$ is 6-chloro, Y is C—$CH_3$ and $R^2$ is methyl and $(R^c)_p$ correspond to one row in Table C Table 140
Compounds of the formula IG, in which $(R^1)_n$ is 6-chloro, Y is C—Cl and $R^2$ is methyl and $(R^c)_p$, correspond to one row in Table C Table 141
Compounds of the formula IG, in which $(R^1)_n$ is 6-methyl, Y is N and $R^2$ is methyl and $(R^c)_p$ correspond to one row in Table C Table 142
Compounds of the formula IG, in which $(R^1)_n$ is 6-methyl, Y is CH and $R^2$ is methyl and $(R^c)_p$ correspond to one row in Table C Table 143
Compounds of the formula IG, in which $(R^1)_n$ is 6-methyl, Y is C—$CH_3$ and $R^2$ is methyl and $(R^c)_p$ correspond to one row in Table C Table 144
Compounds of the formula IG, in which $(R^1)_n$ is 6-methyl, Y is C—Cl and $R^2$ is methyl and $(R^c)_p$ correspond to one row in Table C Table 145
Compounds of the formula IG, in which $(R^1)_n$ is hydrogen, Y is N and $R^2$ is trifluoromethyl and $(R^c)_p$ correspond to one row in Table C Table 146
Compounds of the formula IG, in which $(R^1)_n$ is hydrogen, Y is CH and $R^2$ is trifluoromethyl and $(R^c)_p$ correspond to one row in Table C Table 147
Compounds of the formula IG, in which $(R^1)_n$ is hydrogen, Y is C—$CH_3$ and $R^2$ is trifluoromethyl and $(R^c)_p$ correspond to one row in Table C Table 148
Compounds of the formula IG, in which $(R^1)_n$ is hydrogen, Y is C—Cl and $R^2$ is trifluoromethyl and $(R^c)_p$ correspond to one row in Table C Table 149
Compounds of the formula IG, in which $(R^1)_n$ is 6-chloro, Y is N and $R^2$ is trifluoromethyl and $(R^c)_p$ correspond to one row in Table C Table 150
Compounds of the formula IG, in which $(R^1)_n$ is 6-chloro, Y is CH and $R^2$ is trifluoromethyl and $(R^c)_p$ correspond to one row in Table C Table 151
Compounds of the formula IG, in which $(R^1)_n$ is 6-chloro, Y is C—$CH_3$ and $R^2$ is trifluoromethyl and $(R^c)_p$ correspond to one row in Table C Table 152
Compounds of the formula IG, in which $(R^1)_n$ is 6-chloro, Y is C—Cl and $R^2$ is trifluoromethyl and $(R^c)_p$ correspond to one row in Table C Table 153
Compounds of the formula IG, in which $(R^1)_n$ is 6-methyl, Y is N and $R^2$ is trifluoromethyl and $(R^c)_p$ correspond to one row in Table C Table 154
Compounds of the formula IG, in which $(R^1)_n$ is 6-methyl, Y is CH and $R^2$ is trifluoromethyl and $(R^c)_p$ correspond to one row in Table C Table 155
Compounds of the formula IG, in which $(R^1)_n$ is 6-methyl, Y is C—$CH_3$ and $R^2$ is trifluoromethyl and $(R^c)_p$ correspond to one row in Table C Table 156
Compounds of the formula IG, in which $(R^1)_n$ is 6-methyl, Y is C—Cl and $R^2$ is trifluoromethyl and $(R^c)_p$ correspond to one row in Table C Table 157
Compounds of the formula IH, in which $(R^1)_n$ is hydrogen, Y is N and $R^2$ is hydrogen and $(R^c)_p$ correspond to one row in Table C Table 158
Compounds of the formula IH, in which $(R^1)_n$ is hydrogen, Y is CH and $R^2$ is hydrogen and $(R^c)_p$ correspond to one row in Table C Table 159
Compounds of the formula IH, in which $(R^1)_n$ is hydrogen, Y is C—$CH_3$ and $R^2$ is hydrogen and $(R^c)_p$ correspond to one row in Table C Table 160
Compounds of the formula IH, in which $(R^1)_n$ is hydrogen, Y is C—Cl and R is hydrogen and $(R^c)_p$ correspond to one row in Table C Table 161
Compounds of the formula IH, in which $(R^1)_n$ is 6-chloro, Y is N and $R^2$ is hydrogen and $(R^c)_p$ correspond to one row in Table C Table 162
Compounds of the formula IH, in which $(R^1)_n$ is 6-chloro, Y is CH and $R^2$ is hydrogen and $(R^c)_p$ correspond to one row in Table C Table 163
Compounds of the formula IH, in which $(R^1)_n$ is 6-chloro, Y is C—$CH_3$ and $R^2$ is hydrogen and $(R^c)_p$ correspond to one row in Table C Table 164
Compounds of the formula IH, in which $(R^1)_n$ is 6-chloro, Y is C—Cl and $R^2$ is hydrogen and $(R^c)_p$ correspond to one row in Table C Table 165
Compounds of the formula IH, in which $(R^1)_n$ is 6-methyl, Y is N and $R^2$ is hydrogen and $(R^c)_p$ correspond to one row in Table C Table 166
Compounds of the formula IH, in which $(R^1)_n$ is 6-methyl, Y is CH and $R^2$ is hydrogen and $(R^c)_p$ correspond to one row in Table C Table 167
Compounds of the formula IH, in which $(R1)_n$ is 6-methyl, Y is C—$CH_3$ and $R^2$ is hydrogen and $(R^c)_p$ correspond to one row in Table C Table 168
Compounds of the formula IH, in which $(R^1)_n$ is 6-methyl, Y is C—Cl and $R^2$ is hydrogen and $(R^c)_p$ correspond to one row in Table C Table 169
Compounds of the formula IH, in which $(R^1)_n$ is hydrogen, Y is N and $R^2$ is methyl and $(R^c)_p$ correspond to one row in Table C Table 170
Compounds of the formula IH, in which $(R^1)_n$ is hydrogen, Y is CH and R2 is methyl and $(R^c)_p$ correspond to one row in Table C Table 171
Compounds of the formula IH, in which $(R^1)_n$ is hydrogen, Y is C—$CH_3$ and R is methyl and $(R^c)_p$ correspond to one row in Table C Table 172
Compounds of the formula IH, in which $(R^1)_n$ is hydrogen, Y is C—Cl and $R^2$ is methyl and $(R^c)_p$ correspond to one row in Table C Table 173
Compounds of the formula IH, in which $(R^1)_n$ is 6-chloro, Y is N and $R^2$ is methyl and $(R^c)_p$ correspond to one row in Table C Table 174
Compounds of the formula IH, in which $(R^1)_n$ is 6-chloro, Y is CH and $R^2$ is methyl and $(R^c)_p$ correspond to one row in Table C Table 175
Compounds of the formula IH, in which $(R^1)_n$ is 6-chloro, Y is C—$CH_3$ and $R^2$ is methyl and $(R^c)_p$ correspond to one row in Table C Table 176
Compounds of the formula IH, in which $(R^1)_n$ is 6-chloro, Y is C—Cl and $R^2$ is methyl and $(R^c)_p$ correspond to one row in Table C Table 177
Compounds of the formula IH, in which $(R^1)_n$ is 6-methyl, Y is N and $R^2$ is methyl and $(R^c)_p$ correspond to one row in Table C Table 178
Compounds of the formula IH, in which $(R^1)_n$ is 6-methyl, Y is CH and $R^2$ is methyl and $(R^c)_p$ correspond to one row in Table C Table 179
Compounds of the formula IH, in which $(R^1)_n$ is 6-methyl, Y is C—$CH_3$ and $R^2$ is methyl and $(R^c)_p$ correspond to one row in Table C Table 180
Compounds of the formula IH, in which $(R^1)_n$ is 6-methyl, Y is C—Cl and $R^2$ is methyl and $(R^c)_p$ correspond to one row in Table C Table 181
Compounds of the formula IH, in which $(R^1)_n$ is hydrogen, Y is N and $R^2$ is trifluoromethyl and $(R^c)_p$ correspond to one row in Table C Table 182
Compounds of the formula IH, in which $(R^1)_n$ is hydrogen, Y is CH and $R^2$ is trifluoromethyl and $(R^c)_p$ correspond to one row in Table C Table 183
Compounds of the formula IH, in which $(R^1)_n$ is hydrogen, Y is C—$CH_3$ and $R^2$ is trifluoromethyl and $(R^c)_p$ correspond to one row in Table C Table 184
Compounds of the formula IH, in which $(R^1)_n$ is hydrogen, Y is C—Cl and $R^2$ is trifluoromethyl and $(R^c)_p$ correspond to one row in Table C Table 185
Compounds of the formula IH, in which $(R^1)_n$ is 6-chloro, Y is N and $R^2$ is trifluoromethyl and $(R^c)_p$ correspond to one row in Table C Table 186
Compounds of the formula IH, in which $(R^1)_n$ is 6-chloro, Y is CH and $R^2$ is trifluoromethyl and $(R^c)_p$ correspond to one row in Table C Table 187
Compounds of the formula IH, in which $(R^1)_n$ is 6-chloro, Y is C—$CH_3$ and $R^2$ is trifluoromethyl and $(R^c)_p$ correspond to one row in Table C Table 188
Compounds of the formula IH, in which $(R^1)_n$ is 6-chloro, Y is C—Cl and $R^2$ is trifluoromethyl and $(R^c)_p$ correspond to one row in Table C Table 189
Compounds of the formula IH, in which $(R^1)_n$ is 6-methyl, Y is N and $R^2$ is trifluoromethyl and $(R^c)_p$ correspond to one row in Table C Table 190
Compounds of the formula IH, in which $(R^1)_n$ is 6-methyl, Y is CH and $R^2$ is trifluoromethyl and $(R^c)_p$ mcorrespond to one row in Table C Table 191
Compounds of the formula IH, in which $(R^1)_n$ is 6-methyl, Y is C—$CH_3$ and $R^2$ is trifluoromethyl and $(R^c)_p$ correspond to one row in Table C Table 192
Compounds of the formula IH, in which $(R^1)_n$ is 6-methyl, Y is C—Cl and $R^2$ is trifluoromethyl and $(R^c)_p$ correspond to one row in Table C Table 193
Compounds of the formula IJ, in which $(R^1)_n$ is hydrogen, Y is N and $R^2$ is hydrogen and $(R^c)_p$ correspond to one row in Table C Table 194
Compounds of the formula IJ, in which $(R^1)_n$ is hydrogen, Y is CH and $R^2$ is hydrogen and $(R^c)_p$ correspond to one row in Table C Table 195
Compounds of the formula IJ, in which $(R^1)_n$ is hydrogen, Y is C—$CH_3$ and $R^2$ is hydrogen and $(R^c)_p$ correspond to one row in Table C Table 196
Compounds of the formula IJ, in which $(R^1)_n$ is hydrogen, Y is C—Cl and $R^2$ is hydrogen and $(R^c)_p$ correspond to one row in Table C Table 197
Compounds of the formula IJ, in which $(R^1)_n$ is 6-chloro, Y is N and $R^2$ is hydrogen and $(R^c)_p$ correspond to one row in Table C Table 198
Compounds of the formula IJ, in which $(R^1)_n$ is 6-chloro, Y is CH and $R^2$ is hydrogen and $(R^c)_p$ correspond to one row in Table C Table 199
Compounds of the formula IJ, in which $(R^1)_n$ is 6-chloro, Y is C—$CH_3$ and $R^2$ is hydrogen and $(R^c)_p$ correspond to one row in Table C Table 200
Compounds of the formula IJ, in which $(R^1)_n$ is 6-chloro, Y is C—Cl and $R^2$ is hydrogen and $(R^c)_p$ correspond to one row in Table C Table 201
Compounds of the formula IJ, in which $(R^1)_n$ is 6-methyl, Y is N and $R^2$ is hydrogen and $(R^c)_p$ correspond to one row in Table C Table 202
Compounds of the formula IJ, in which $(R^1)_n$ is 6-methyl, Y is CH and $R^2$ is hydrogen and $(R^c)_p$ correspond to one row in Table C Table 203
Compounds of the formula IJ, in which $(R^1)_n$ is 6-methyl, Y is C—$CH_3$ and $R^2$ is hydrogen and $(R^c)_p$ correspond to one row in Table C Table 204
Compounds of the formula IJ, in which $(R^1)_n$ is 6-methyl, Y is C—Cl and $R^2$ is hydrogen and $(R^c)_p$ correspond to one row in Table C Table 205
Compounds of the formula IJ, in which $(R^1)_n$ is hydrogen, Y is N and $R^2$ is methyl and $(R^c)_p$ correspond to one row in Table C Table 206
Compounds of the formula IJ, in which $(R^1)_n$ is hydrogen, Y is CH and $R^2$ is methyl and $(R^c)_p$ correspond to one row in Table C Table 207
Compounds of the formula IJ, in which $(R^1)_n$ is hydrogen, Y is C—$CH_3$ and $R^2$ is methyl and $(R^c)_p$ correspond to one row in Table C Table 208
Compounds of the formula IJ, in which $(R^1)_n$ is hydrogen, Y is C—Cl and $R^2$ is methyl and $(R^c)_p$ correspond to one row in Table C Table 209
Compounds of the formula IJ, in which $(R^1)_n$ is 6-chloro, Y is N and $R^2$ is methyl and $(R^c)_p$ correspond to one row in Table C Table 210
Compounds of the formula IJ, in which $(R^1)_n$ is 6-chloro, Y is CH and $R^2$ is methyl and $(R^c)_p$ correspond to one row in Table C Table 211
Compounds of the formula IJ, in which $(R^1)_n$ is 6-chloro, Y is C—$CH_3$ and $R^2$ is methyl and $(R^c)_p$ correspond to one row in Table C Table 212
Compounds of the formula IJ, in which $(R^1)_n$ is 6-chloro, Y is C—Cl and $R^2$ is methyl and $(R^c)_p$ correspond to one row in Table C Table 213
Compounds of the formula IJ, in which $(R^1)_n$ is 6-methyl, Y is N and $R^2$ is methyl and $(R^c)_p$ correspond to one row in Table C Table 214
Compounds of the formula IJ, in which $(R^1)_n$ is 6-methyl, Y is CH and $R^2$ is methyl and $(R^c)_p$ correspond to one row in Table C Table 215
Compounds of the formula IJ, in which $(R^1)_n$ is 6-methyl, Y is C—$CH_3$ and $R^2$ is methyl and $(R^c)_p$ correspond to one row in Table C Table 216
Compounds of the formula IJ, in which $(R^1)_n$ is 6-methyl, Y is C—Cl and $R^2$ is methyl and $(R^c)_p$ correspond to one row in Table C Table 217
Compounds of the formula IJ, in which $(R^1)_n$ is hydrogen, Y is N and R is trifluoromethyl and $(R^c)_p$ correspond to one row in Table C Table 218
Compounds of the formula IJ, in which $(R^1)_n$ is hydrogen, Y is CH and $R^2$ is trifluoromethyl and $(R^c)_p$ correspond to one row in Table C Table 219
Compounds of the formula IJ, in which $(R^1)_n$ is hydrogen, Y is C—$CH_3$ and $R^2$ is trifluoromethyl and $(R^c)_p$ correspond to one row in Table C Table 220
Compounds of the formula IJ, in which $(R^1)_n$ is hydrogen, Y is C—Cl and $R^2$ is trifluoromethyl and $(R^c)_p$ correspond to one row in Table C Table 221
Compounds of the formula IJ, in which $(R^1)_n$ is 6-chloro, Y is N and $R^2$ is trifluoromethyl and $(R^c)_p$ correspond to one row in Table C Table 222
Compounds of the formula IJ, in which $(R^1)_n$ is 6-chloro, Y is CH and $R^2$ is trifluoromethyl and $(R^c)_p$ correspond to one row in Table C Table 223
Compounds of the formula IJ, in which $(R^1)_n$ is 6-chloro, Y is C—$CH_3$ and $R^2$ is trifluoromethyl and $(R^c)_p$ correspond to one row in Table C Table 224
Compounds of the formula IJ, in which $(R^1)_n$ is 6-chloro, Y is C—Cl and $R^2$ is trifluoromethyl and $(R^c)_p$ correspond to one row in Table C Table 225
Compounds of the formula IJ, in which $(R^1)_n$ is 6-methyl, Y is N and $R^2$ is trifluoromethyl and $(R^c)_p$ correspond to one row in Table C Table 226
Compounds of the formula IJ, in which $(R^1)_n$ is 6-methyl, Y is CH and $R^2$ is trifluoromethyl and $(R^c)_p$ correspond to one row in Table C Table 227
Compounds of the formula IJ, in which $(R^1)_n$ is 6-methyl, Y is C—$CH_3$ and $R^2$ is trifluoromethyl and $(R^c)_p$ correspond to one row in Table C Table 228
Compounds of the formula IJ, in which $(R^1)_n$ is 6-methyl, Y is C—Cl and $R^2$ is trifluoromethyl and $(R^c)_p$ correspond to one row in Table C

TABLE A

| No. | $(R^1)_n$ | $R^2$ | $R^3$ |
|---|---|---|---|
| A-1 | H | H | cyclohexyl |
| A-2 | H | H | benzyl |
| A-3 | H | H | phenyl |
| A-4 | H | H | 2-pyridyl |
| A-5 | H | H | 5-Cl-pyridyl-2 |
| A-6 | H | H | 5-$CF_3$-pyridyl-2 |
| A-7 | H | H | 2-pyrazinyl |
| A-8 | H | $CH_3$ | cyclohexyl |
| A-9 | H | $CH_3$ | benzyl |
| A-10 | H | $CH_3$ | phenyl |
| A-11 | H | $CH_3$ | 2-pyridyl |
| A-12 | H | $CH_3$ | 5-Cl-pyridyl-2 |
| A-13 | H | $CH_3$ | 5-$CF_3$-pyridyl-2 |
| A-14 | H | $CH_3$ | 2-pyrazinyl |
| A-15 | 6-Cl | H | cyclohexyl |
| A-16 | 6-Cl | H | benzyl |
| A-17 | 6-Cl | H | phenyl |
| A-18 | 6-Cl | H | 2-pyridyl |
| A-19 | 6-Cl | H | 5-Cl-pyridyl-2 |
| A-20 | 6-Cl | H | 5-$CF_3$-pyridyl-2 |
| A-21 | 6-Cl | H | 2-pyrazinyl |
| A-22 | 6-Cl | $CH_3$ | cyclohexyl |
| A-23 | 6-Cl | $CH_3$ | benzyl |
| A-24 | 6-Cl | $CH_3$ | phenyl |
| A-25 | 6-Cl | $CH_3$ | 2-pyridyl |
| A-26 | 6-Cl | $CH_3$ | 5-Cl-pyridyl-2 |
| A-27 | 6-Cl | $CH_3$ | 5-$CF_3$-pyridyl-2 |
| A-28 | 6-Cl | $CH_3$ | 2-pyrazinyl |
| A-29 | 6-$CH_3$ | H | cyclohexyl |
| A-30 | 6-$CH_3$ | H | benzyl |
| A-31 | 6-$CH_3$ | H | phenyl |
| A-32 | 6-$CH_3$ | H | 2-pyridyl |
| A-33 | 6-$CH_3$ | H | 5-Cl-pyridyl-2 |
| A-34 | 6-$CH_3$ | H | 5-$CF_3$-pyridyl-2 |
| A-35 | 6-$CH_3$ | H | 2-pyrazinyl |
| A-36 | 6-$CH_3$ | $CH_3$ | cyclohexyl |
| A-37 | 6-$CH_3$ | $CH_3$ | benzyl |
| A-38 | 6-$CH_3$ | $CH_3$ | phenyl |
| A-39 | 6-$CH_3$ | $CH_3$ | 2-pyridyl |
| A-40 | 6-$CH_3$ | $CH_3$ | 5-Cl-pyridyl-2 |
| A-41 | 6-$CH_3$ | $CH_3$ | 5-$CF_3$-pyridyl-2 |
| A-42 | 6-$CH_3$ | $CH_3$ | 2-pyrazinyl |

TABLE B

| No. | $(R^c)_p$ |
|---|---|
| B-1 | H |
| B-2 | 2-F |
| B-3 | 3-F |
| B-4 | 4-F |
| B-5 | 2,4-$F_2$ |
| B-6 | 2,4,6-$F_3$ |
| B-7 | 2,3,4,5,6-$F_5$ |
| B-8 | 2,3-$F_2$ |
| B-9 | 2-Cl |
| B-10 | 3-Cl |
| B-11 | 4-Cl |
| B-12 | 2,3-$Cl_2$ |
| B-13 | 2,4-$Cl_2$ |
| B-14 | 2,5-$Cl_2$ |
| B-15 | 2,6-$Cl_2$ |
| B-16 | 3,4-$Cl_2$ |
| B-17 | 3,5-$Cl_2$ |
| B-18 | 2,3,4-$Cl_3$ |
| B-19 | 2,3,5-$Cl_3$ |
| B-20 | 2,3,6-$Cl_3$ |
| B-21 | 2,4,5-$Cl_3$ |
| B-22 | 2,4,6-$Cl_3$ |
| B-23 | 3,4,5-$Cl_3$ |
| B-24 | 2,3,4,6-$Cl_4$ |
| B-25 | 2,3,5,6-$Cl_4$ |
| B-26 | 2,3,4,5,6-$Cl_5$ |
| B-27 | 2-Br |
| B-28 | 3-Br |
| B-29 | 4-Br |
| B-30 | 2,4-$Br_2$ |
| B-31 | 2,5-$Br_2$ |
| B-32 | 2,6-$Br_2$ |
| B-33 | 2,4,6-$Br_3$ |
| B-34 | 2,3,4,5,6-$Br_5$ |
| B-35 | 2-J |
| B-36 | 3-J |
| B-37 | 4-J |
| B-38 | 2,4-$J_2$ |
| B-39 | 2-Cl, 3-F |
| B-40 | 2-Cl, 4-F |
| B-41 | 2-Cl, 5-F |
| B-42 | 2-Cl, 6-F |
| B-43 | 2-Cl, 3-Br |
| B-44 | 2-Cl, 4-Br |
| B-45 | 2-Cl, 5-Br |
| B-46 | 2-Cl, 6-Br |
| B-47 | 2-Br, 3-Cl |
| B-48 | 2-Br, 4-Cl |
| B-49 | 2-Br, 5-Cl |
| B-50 | 2-Br, 3-F |
| B-51 | 2-Br, 4-F |
| B-52 | 2-Br, 5-F |
| B-53 | 2-Br, 6-F |
| B-54 | 2-F, 3-Cl |
| B-55 | 2-F, 4-Cl |
| B-56 | 2-F, 5-Cl |
| B-57 | 3-Cl, 4-F |
| B-58 | 3-Cl, 5-F |
| B-59 | 3-Cl, 4-Br |
| B-60 | 3-Cl, 5-Br |
| B-61 | 3-F, 4-Cl |
| B-62 | 3-F, 4-Br |
| B-63 | 3-Br, 4-Cl |
| B-64 | 3-Br, 4-F |
| B-65 | 2,6-$Cl_2$, 4-Br |
| B-66 | 2-$CH_3$ |
| B-67 | 3-$CH_3$ |
| B-68 | 4-$CH_3$ |
| B-69 | 2,3-$(CH_3)_2$ |
| B-70 | 2,4-$(CH_3)_2$ |
| B-71 | 2,5-$(CH_3)_2$ |
| B-72 | 2,6-$(CH_3)_2$ |
| B-73 | 3,4-$(CH_3)_2$ |
| B-74 | 3,5-$(CH_3)_2$ |
| B-75 | 2,3,5-$(CH_3)_3$ |
| B-76 | 2,3,4-$(CH_3)_3$ |
| B-77 | 2,3,6-$(CH_3)_3$ |
| B-78 | 2,4,5-$(CH_3)_3$ |
| B-79 | 2,4,6-$(CH_3)_3$ |

TABLE B-continued

| No. | $(R^c)_p$ |
|---|---|
| B-80 | 3,4,5-$(CH_3)_3$ |
| B-81 | 2,3,4,6-$(CH_3)_4$ |
| B-82 | 2,3,5,6-$(CH_3)_4$ |
| B-83 | 2,3,4,5,6-$(CH_3)_5$ |
| B-84 | 2-$C_2H_5$ |
| B-85 | 3-$C_2H_5$ |
| B-86 | 4-$C_2H_5$ |
| B-87 | 2,4-$(C_2H_5)_5$ |
| B-88 | 2,6-$(C_2H_5)_2$ |
| B-89 | 3,5-$(C_2H_5)_2$ |
| B-90 | 2,4,6-$(C_2H_5)_3$ |
| B-91 | 2-n-$C_3H_7$ |
| B-92 | 3-n-$C_3H_7$ |
| B-93 | 4-n-$C_3H_7$ |
| B-94 | 2-i-$C_3H_7$ |
| B-95 | 3-i-$C_3H_7$ |
| B-96 | 4-i-$C_3H_7$ |
| B-97 | 2,4-(i-$C_3H_7)_2$ |
| B-98 | 2,6-(i-$C_3H_7)_2$ |
| B-99 | 3,5-(i-$C_3H_7)_2$ |
| B-100 | 2-s-$C_4H_9$ |
| B-101 | 3-s-$C_4H_9$ |
| B-102 | 4-s-$C_4H_9$ |
| B-103 | 2-t-$C_4H_9$ |
| B-104 | 3-t-$C_4H_9$ |
| B-105 | 4-t-$C_4H_9$ |
| B-106 | 4-n-$C_4H_9$ |
| B-107 | 2-$CH_3$, 4-t-$C_4H_9$ |
| B-108 | 2-$CH_3$, 6-t-$C_4H_9$ |
| B-109 | 2-$CH_3$, 4-i-$C_3H_7$ |
| B-110 | 2-$CH_3$, 5-i-$C_3H_7$ |
| B-111 | 3-$CH_3$, 4-i-$C_3H_7$ |
| B-112 | 2-cyclo-$C_6H_{11}$ |
| B-113 | 3-cyclo-$C_6H_{11}$ |
| B-114 | 4-cyclo-$C_6H_{11}$ |
| B-115 | 2-Cl, 4-$C_6H_5$ |
| B-116 | 2-Br, 4-$C_6H_5$ |
| B-117 | 2-$OCH_3$ |
| B-118 | 3-$OCH_3$ |
| B-119 | 4-$OCH_3$ |
| B-120 | 2-$OC_2H_5$ |
| B-121 | 3-O-$C_2H_5$ |
| B-122 | 4-O-$C_2H_5$ |
| B-123 | 2-O-n-$C_3H_7$ |
| B-124 | 3-O-n-$C_3H_7$ |
| B-125 | 4-O-n-$C_3H_7$ |
| B-126 | 2-O-i-$C_3H_7$ |
| B-127 | 3-O-i-$C_3H_7$ |
| B-128 | 4-O-i-$C_3H_7$ |
| B-129 | 2-O-n-$C_6H_{13}$ |
| B-130 | 3-O-n-$C_6H_{13}$ |
| B-131 | 4-O-n-$C_6H_{13}$ |
| B-132 | 2-O-$CH_2C_6H_5$ |
| B-133 | 3-O-$CH_2C_6H_5$ |
| B-134 | 4-O-$CH_2C_6H_5$ |
| B-135 | 2-O-$(CH_2)_3C_6H_5$ |
| B-136 | 4-O-$(CH_2)_3C_6H_5$ |
| B-137 | 2,3-$(OCH_3)_2$ |
| B-138 | 2,4-$(OCH_3)_2$ |
| B-139 | 2,5-$(OCH_3)_2$ |
| B-140 | 2,6-$(OCH_3)_2$ |
| B-141 | 3,4-$(OCH_3)_2$ |
| B-142 | 3,5-$(OCH_3)_2$ |
| B-143 | 2-O-t-$C_4H_9$ |
| B-144 | 3-O-t-$C_4H_9$ |
| B-145 | 4-O-t-$C_4H_9$ |
| B-146 | 3-(3'-Cl-$C_6H_4$) |
| B-147 | 4-(4'-$CH_3$-$C_6H_4$) |
| B-148 | 2-O-$C_6H_5$ |
| B-149 | 3-O-$C_6H_5$ |
| B-150 | 4-O-$C_6H_5$ |
| B-151 | 2-O-(2'-F-$C_6H_4$) |
| B-152 | 3-O-(3'-Cl-$C_6H_4$) |
| B-153 | 4-O-(4'-$CH_3$-$C_6H_4$) |
| B-154 | 2,3,6-$(CH_3)_3$, 4-F |
| B-155 | 2,3,6-$(CH_3)_3$, 4-Cl |
| B-156 | 2,3,6-$(CH_3)_3$, 4-Br |
| B-157 | 2,4-$(CH_3)_2$, 6-F |
| B-158 | 2,4-$(CH_3)_2$, 6-Cl |
| B-159 | 2,4-$(CH_3)_2$, 6-Br |
| B-160 | 2-i-$C_3H_7$, 4-Cl, 5-$CH_3$ |
| B-161 | 2-Cl, 4-$NO_2$ |
| B-162 | 2-$NO_2$, 4-Cl |
| B-163 | 2-$OCH_3$, 5-$NO_2$ |
| B-164 | 2,4-$Cl_2$, 5-$NO_2$ |
| B-165 | 2,4-$Cl_2$, 6-$NO_2$ |
| B-166 | 2,6-$Cl_2$, 4-$NO_2$ |
| B-167 | 2,6-$Br_2$, 4-$NO_2$ |
| B-168 | 2,6-$J_2$, 4-$NO_2$ |
| B-169 | 2-$CH_3$, 5-i-$C_3H_7$, 4-Cl |
| B-170 | 2-$CO_2CH_3$ |
| B-171 | 3-$CO_2CH_3$ |
| B-172 | 4-$CO_2CH_3$ |
| B-173 | 2-$CH_2$-$OCH_3$ |
| B-174 | 3-$CH_2$-$OCH_3$ |
| B-175 | 4-$CH_2$-$OCH_3$ |
| B-176 | 2-Me-4-$CH_3$-$CH(CH_3)$-CO |
| B-177 | 2-$CH_3$-4-(C[CH] = $NOCH_3$) |
| B-178 | 2-$CH_3$-4-(C[CH] = $NOC_2H_5$) |
| B-179 | 2-$CH_3$-4-(C[CH] = NO-n-$C_3H_7$) |
| B-180 | 2-$CH_3$-4-(C[CH] = NO-i-$C_3H_7$) |
| B-181 | 2,5-$(CH_3)_2$-4-(C[CH] = $NOCH_3$) |
| B-182 | 2,5-$(CH_3)_2$-4-(C[CH] = $NOC_2H_5$) |
| B-183 | 2,5-$(CH_3)_2$-4-(C[CH] = NO-n-$C_3H_7$) |
| B-184 | 2,5-$(CH_3)_2$-4-(C[CH] = NO-i-$C_3H_7$) |
| B-185 | 2-$C_6H_5$ |
| B-186 | 3-$C_6H_5$ |
| B-187 | 4-$C_6H_5$ |
| B-188 | 2-(2'-F-$C_6H_4$) |
| B-189 | 2-$CH_3$, 5-Br |
| B-190 | 2-$CH_3$, 6-Br |
| B-191 | 2-Cl, 3-$CH_3$ |
| B-192 | 2-Cl, 4-$CH_3$ |
| B-193 | 2-Cl, 5-$CH_3$ |
| B-194 | 2-F, 3-$CH_3$ |
| B-195 | 2-F, 4-$CH_3$ |
| B-196 | 2-F, 5-$CH_3$ |
| B-197 | 2-Br, 3-$CH_3$ |
| B-198 | 2-Br, 4-$CH_3$ |
| B-199 | 2-Br, 5-$CH_3$ |
| B-200 | 3-$CH_3$, 4-Cl |
| B-201 | 3-$CH_3$, 5-Cl |
| B-202 | 3-$CH_3$, 4-F |
| B-203 | 3-$CH_3$, 5-F |
| B-204 | 3-$CH_3$, 4-Br |
| B-205 | 3-$CH_3$, 5-Br |
| B-206 | 3-F, 4-$CH_3$ |
| B-207 | 3-Cl, 4-$CH_3$ |
| B-208 | 3-Br, 4-$CH_3$ |
| B-209 | 2-Cl, 4,5-$(CH_3)_2$ |
| B-210 | 2-Br, 4,5-$(CH_3)_2$ |
| B-211 | 2-Cl, 3,5-$(CH_3)_2$ |
| B-212 | 2-Br, 3,5-$(CH_3)_2$ |
| B-213 | 2,6-$Cl_2$, 4-$CH_3$ |
| B-214 | 2,6-$F_2$, 4-$CH_3$ |
| B-215 | 2,6-$Br_2$, 4-$CH_3$ |
| B-216 | 2,4-$Br_2$, 6-$CH_3$ |
| B-217 | 2,4-$F_2$, 6-$CH_3$ |
| B-218 | 2,4-$Br_2$, 6-$CH_3$ |
| B-219 | 2,6-$(CH_3)_2$, 4-F |
| B-220 | 2,6-$(CH_3)_2$, 4-Cl |
| B-221 | 2,6-$(CH_3)_2$, 4-Br |
| B-222 | 3,5-$(CH_3)_2$, 4-F |
| B-223 | 3,5-$(CH_3)_2$, 4-Cl |
| B-224 | 3,5-$(CH_3)_2$, 4-Br |
| B-225 | 2-$CF_3$ |
| B-226 | 3-$CF_3$ |
| B-227 | 4-$CF_3$ |
| B-228 | 2-$OCF_3$ |
| B-229 | 3-$OCF_3$ |
| B-230 | 4-$OCF_3$ |
| B-231 | 3-$OCH_2CHF_2$ |
| B-232 | 2-$NO_2$ |
| B-233 | 3-$NO_2$ |

TABLE B-continued

| No. | (R$^c$)$_p$ |
| --- | --- |
| B-234 | 4-NO$_2$ |
| B-235 | 2-CN |
| B-236 | 3-CN |
| B-237 | 4-CN |
| B-238 | 2-CH$_3$, 3-Cl |
| B-239 | 2-CH$_3$, 4-Cl |
| B-240 | 2-CH$_3$, 5-Cl |
| B-241 | 2-CH$_3$, 6-Cl |
| B-242 | 2-CH$_3$, 3-F |
| B-243 | 2-CH$_3$, 4-F |
| B-244 | 2-CH$_3$, 5-F |
| B-245 | 2-CH$_3$, 6-F |
| B-246 | 2-CH$_3$, 3-Br |
| B-247 | 2-CH$_3$, 4-Br |
| B-248 | 2-pyridyl-2' |
| B-249 | 3-pyridyl-3' |
| B-250 | 4-pyridyl-4' |

TABLE C

| No. | (R$^c$)$_p$ |
| --- | --- |
| C-1 | 3-Cl |
| C-2 | 4-Cl |
| C-3 | 5-Cl |
| C-4 | 6-Cl |
| C-5 | 3-Br |
| C-6 | 4-Br |
| C-7 | 5-Br |
| C-8 | 6-Br |
| C-9 | 3-F |
| C-10 | 4-F |
| C-11 | 5-F |
| C-12 | 6-F |
| C-13 | 3-CF$_3$ |
| C-14 | 4-CF$_3$ |
| C-15 | 5-CF$_3$ |
| C-16 | 6-CF$_3$ |
| C-17 | 3-CH$_3$ |
| C-18 | 4-CH$_3$ |
| C-19 | 5-CH$_3$ |
| C-20 | 6-CH$_3$ |
| C-21 | 3-OCH$_3$ |
| C-22 | 4-OCH$_3$ |
| C-23 | 5-OCH$_3$ |
| C-24 | 6-OCH$_3$ |
| C-25 | 3-OCF$_3$ |
| C-26 | 4-OCF$_3$ |
| C-27 | 5-OCF$_3$ |
| C-28 | 6-OCF$_3$ |
| C-29 | 5-CF$_3$-6-Cl |

The compounds I are suitable as fungicides. They have outstanding activity against a broad spectrum of phytopathogenic fungi, in particular from the classes of the Ascomycetes, Deuteromycetes, Phycomycetes and Basidiomycetes. Some of them act systemically, and they can be employed in crop protection as foliar- and soil-acting fungicides.

They are especially important for controlling a large number of fungi on a variety of crop plants such as wheat, rye, barley, oats, rice, maize, grass, bananas, cotton, soya, coffee, sugar cane, grapevines, fruit species, ornamentals and vegetables such as cucumbers, beans, tomatoes, potatoes and cucurbits, and on the seeds of these plants.

Specifically, they are suitable for controlling the following plant diseases:

Alternaria species on vegetables and fruit, *Botrytis cinerea* (gray mold) on strawberries, vegetables, ornamentals and grapevines, *Cercospora arachidicola* on peanuts, *Erysiphe cichoracearum* and *Sphaerotheca fuliginea* on cucurbits, *Erysiphe graminis* (powdery mildew) on cereals, Fusarium and Verticillium species on various plants, Helminthosporium species on cereals, Mycosphaerella species on bananas and peanuts, *Phytophthora infestans* on potatoes and tomatoes, *Plasmopara viticola* on grapevines, *Podosphaera leucotricha* on apples, *Pseudocercosporella herpotrichoides* on wheat and barley, Pseudoperonospora species on hops and cucumbers, Puccinia species on cereals, *Pyricularia oryzae* on rice, Rhizoctonia species on cotton, rice and lawns, *Septoria nodorum* on wheat, *Uncinula necator* on grapevines, Ustilago species on cereals and sugar cane, and Venturia species (scab) on apples and pears.

Moreover, the compounds I are suitable for controlling harmful fungi such as Paecilomyces variotii in the protection of materials (e.g. wood, paper, paint dispersions, fibers and tissues) and in the protection of stored products.

The compounds I are applied by treating the fungi, or the plants, seeds, materials or the soil to be protected against fungal infection, with a fungicidally active amount of the active ingredients. Application can be effected both before and after infection of the materials, plants or seeds by the fungi.

In general, the fungicidal compositions comprise from 0.1 to 95, preferably 0.5 to 90, % by weight of active ingredient.

When used in crop protection, the rates of application are from 0.01 to 2.0 kg of active ingredient per ha, depending on the nature of the effect desired.

In the treatment of seed, amounts of active ingredient of from 0.001 to 0.1 g, preferably 0.01 to 0.05 g, are generally required per kilogram of seed.

When used in the protection of materials or stored products, the rate of application of active ingredient depends on the nature of the field of application and on the effect desired. Rates of application conventionally used in the protection of materials are, for example, from 0.001 g to 2 kg, preferably 0.005 g to 1 kg, of active ingredient per cubic meter of material treated.

Moreover, the compounds of the formula I are suitable for efficiently controlling animal pests from the classes of the insects, arachnids and nematodes. They can be employed in crop protection and in the hygiene, stored-product and veterinary sector for controlling animal pests. In particular, they are suitable for controlling the following animal pests: insects from the order of the *lepidopterans* (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena* scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni and Zeiraphera canadensis, beetles (Coleoptera), for example Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus and Sitophilus granaria, dipterans (Diptera), for example Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea and Tipula paludosa, thrips (Thysanoptera), e.g. Frankliniella fusca, Frankliniella occidentalis, Frankliniella tritici, Scirtothrips citri, Thrips oryzae, Thrips palmi and Thrips tabaci, hymenopterans (Hymenoptera), e.g. Athalia rosae, Atta cephalotes, Atta sexdens, Atta texana, Hoplocampa minuta, Hoplocampa testudinea, Monomorium pharaonis, Solenopsis geminata and Solenopsis invicta, heteropterans (Heteroptera), e.g. Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis and Thyanta perditor, homopterans (Homoptera), e.g. Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dysaphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum and Viteus vitifolii, termites (Isoptera), e.g. Calotermes flavicollis, Leucotermes flavipes, Reticulitermes lucifugus und Termes natalensis, orthopterans (Orthoptera), e.g. Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus and Tachycines asynamorus, Arachnoidea, such as arachnids (Acarina), e.g. Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobius megnini, Paratetranychus pilosus, Dermanyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius and Tetranychus urticae, nematodes such as root knot nematodes, e.g. Meloidogyne hapla, Meloidogyne incognita, Meloidogyne javanica, cyst-forming nematodes, e.g. Globodera rostochiensis, Heterodera avenae, Heterodera glycines, Heterodera schachtii, Heterodera trifolii, stem eelworms and foliar nematodes, e.g. Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus and Pratylenchus goodeyi.

The rate of application of active ingredient for controlling animal pests is from 0.1 to 2.0, preferably 0.2 to 1.0, kg/ha under field conditions.

The compounds I can be converted into the customary formulations, e.g. solutions, emulsions, suspensions, dusts, powders, pastes and granules. The use form depends on the particular purpose; in any case, it should guarantee a fine and uniform distribution of the compound according to the invention.

The formulations are prepared in a known manner, e.g. by extending the active ingredient with solvents and/or carriers, if desired using emulsifiers and dispersants, it also being possible to use other organic solvents as auxiliary solvents if water is used as the diluent. Auxiliaries which are suitable are essentially: solvents such as aromatics (e.g. xylene), chlorinated aromatics (e.g. chlorobenzenes), paraffins (e.g. mineral oil fractions), alcohols (e.g. methanol, butanol), ketones (e.g. cyclohexanone), amines (e.g. ethanolamine, dimethylformamide) and water; carriers such as ground natural minerals (e.g. kaolins, clays, talc, chalk) and ground synthetic minerals (e.g. highly-disperse silica, silicates); emulsifiers such as non-ionic and anionic emulsifiers (e.g. polyoxyethylene fatty alcohol ethers, alkylsulfonates and arylsulfonates) and dispersants such as lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates and fatty acids and their alkali metal and alkaline earth metal salts, salts of sulfated fatty alcohol glycol ether, condensates of sulfonated naphthalene and naphthalene derivatives with formaldehyde, condensates of naphthalene or of napthalenesulfonic acid with phenol or formaldehyde, polyoxyethylene octylphenyl ether, ethoxylated isooctylphenol, octylphenol, nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, e.g. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, e.g. dimethylformamide, dimethyl sulfoxide, N-methylpyrrolidone and water.

Powders, materials for scattering and dusts can be prepared by mixing or concomitantly grinding the active substances with a solid carrier.

Granules, e.g. coated granules, impregnated granules and homogeneous granules, can be prepared by binding the active ingredients to solid carriers. Examples of solid carriers are mineral earths, such as silicas, silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, e.g. ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise of from 0.01 to 95% by weight, preferably from 0.1 to 90% by weight, of the active ingredient. The active ingredients are employed in a purity of from 90% to 100%, preferably 95% to 100% (according to NMR spectrum).

The following are exemplary formulations:

I. 5 parts by weight of a compound according to the invention are mixed intimately with 95 parts by weight of finely divided kaolin. This gives a dust which comprises 5% by weight of the active ingredient.

II. 30 parts by weight of a compound according to the invention are mixed intimately with a mixture of 92 parts by weight of pulverulent silica gel and 8 parts by weight of paraffin oil which had been sprayed onto the surface of this silica gel. This gives a formulation of the active ingredient with good adhesion properties (comprises 23% by weight of active ingredient).

III. 10 parts by weight of a compound according to the invention are dissolved in a mixture composed of 90 parts by weight of xylene, 6 parts by weight of the adduct of 8 to 10 mol of ethylene oxide and 1 mol of oleic acid N-monoethanolamide, 2 parts by weight of calcium dodecylbenzenesulfonate and 2 parts by weight of the adduct of 40 mol of ethylene oxide and 1 mol of castor oil (comprises 9% by weight of active ingredient).

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide and 1 mol of isooctylphenol and 5 parts by weight of the adduct of 40 mol of ethylene oxide and 1 mol of castor oil (comprises 16% by weight of active ingredient).

V. 80 parts by weight of a compound according to the invention are mixed thoroughly with 3 parts by weight of sodium diisobutylnaphthalene-alpha-sulfonate, 10 parts by weight of the sodium salt of a lignosulfonic acid from a sulfite waste liquor and 7 parts by weight of pulverulent silica gel, and the mixture is ground in a hammer mill (comprises 80% by weight of active ingredient).

VI. 90 parts by weight of a compound according to the invention are mixed with 10 parts by weight of N-methyl-$\square$-pyrrolidone, which gives a solution which is suitable for use in the form of microdrops (comprises 90% by weight of active ingredient).

VII. 20 parts by weight of a compound according to the invention are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

VIII. 20 parts by weight of a compound according to the invention are mixed thoroughly with 3 parts by weight of sodium diisobutylnaphthalene-$\square$-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

The active ingredients can be used as such, in the form of their formulations or the use forms prepared therefrom, e.g. in the form of directly sprayable solutions, powders, suspensions or dispersions, emulsions, oil dispersions, pastes, dusts, materials for spreading, or granules, by means of spraying, atomizing, dusting, scattering or pouring. The use forms depend entirely on the intended purposes; in any case, this is intended to guarantee the finest possible distribution of the active ingredients according to the invention.

Aqueous use forms can be prepared from emulsion concentrates, pastes or wettable powders (sprayable powders, oil dispersions) by adding water. To prepare emulsions, pastes or oil dispersions, the substances as such or dissolved in an oil or solvent, can be homogenized in water by means of wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active ingredient concentrations in the ready-to-use products can be varied within substantial ranges. In general, they are from 0.0001 to 10%, preferably from 0.01 to 1%.

The active ingredients may also be used successfully in the ultra-low-volume process (ULV), it being possible to apply formulations comprising over 95% by weight of active ingredient, or even the active ingredient without additives.

Various types of oils, herbicides, fungicides, other pesticides, or bactericides may be added to the active ingredients, if appropriate also only immediately prior to use (tank mix). These agents can be admixed with the agents according to the invention in a weight ratio of 1:10 to 10:1.

In the use form as fungicides, the compositions according to the invention can also be present together with other active ingredients, e.g. with herbicides, insecticides, growth regulators, fungicides or else with fertilizers. Mixing the compounds I or the compositions comprising them in the use form as fungicides with other fungicides frequently results in a broader fungicidal spectrum of action.

The following list of fungicides, together with which the compounds according to the invention can be used, is intended to illustrate the possible combinations, but not to impose any limitation:

sulfur, dithiocarbamates and their derivatives, such as iron (III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis (thiocarbamoyl)disulfide; nitro derivatives, such as dinitro(1-methylheptyl)phenyl crotonate, 2-sec-butyl-4,6-dinitrophenyl 3,3-dimethylacrylate, 2-sec-butyl-4,6-dinitrophenylisopropyl carbonate, diisopropyl 5-nitro-isophthalate; heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis (dimethylamino)phosphinyl]-3-phenyl-1,2,4-triazole, 2,3-dicyano-1,4-dithioanthraquinone, 2-thio-1,3-dithiolo [4,5-b]quinoxaline, methyl 1-(butylcarbamoyl)-2-benzimidazolecarbamate, 2-methoxycarbonylaminobenzimidazole, 2-(2-furyl) benzimidazole, 2-(4-thiazolyl)benzimidazole, N-(1,1,2,2-tetrachloroethylthio)tetrahydrophthalimide, N-trichloromethylthiotetrahydrophthalimide, N-trichloromethylthiophthalimide, N-dichlorofluoromethylthio-N',N'-dimethyl-N-phenylsulfo-diamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thiol 1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl- 2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis-1-(2,2,2-trichloroethyl)formamide, 1-(3,4-dichloroanilino)-1-formylamino-2,2,2-trichloroethane; 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethyl-morpholine, N-[3-(p-tert-butylphenyl)-2-methylpropyl]-piperidine, 1-[2-(2,4-dichlorophenyl)-4-ethyl-1,3-dioxolan-2-yl-ethyl]-1H-1,2,4-triazole, 1-[2-(2,4-dichlorophenyl)-4-n-propyl-1,3-dioxolan-2-yl-ethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, (2RS,3RS)-1-[3-(2-chlorophenyl)-2-(4-fluorophenyl)-oxiran-2-ylmethyl]-1H-1,2,4-triazole, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, strobilurines such as methyl E-methoxyimino-[α-(o-tolyloxy)-o-tolyl] acetate, methyl E-2-{2-[6-(2-cyanophenoxy)pyrimidin-4-yloxy]-phenyl}-3-methoxyacrylate, methyl-E-methoxyimino-[α-(2 -phenoxyphenyl)]-acetamide, methyl E-methoxyimino-[α-(2,5-dimethylphenoxy)-o-tolyl]acetamide, anilinopyrimidines such as N-(4,6-dimethylpyrimidin-2-yl)aniline, N-[4-methyl-6-(1-propynyl)pyrimidin-2-yl]-aniline, N-[4-methyl-6-cyclopropylpyrimidin-2-yl]aniline, phenylpyrroles such as 4-(2,2-difluoro-1,3-benzodioxol-4-yl)pyrrole-3-carbonitrile, cinnamamides such as 3-(4-chlorophenyl)-3-(3,4-dimethoxyphenyl)acryloylmorpholine, and a variety of fungicides such as dodecylguanidine acetate, 3-[3-(3, 5-dimethyl-2-oxycyclohexyl)-2-hydroxyethyl]glutar-imide, hexachlorobenzene, methyl N-(2,6-dimethylphenyl)-N-(2-furoyl)-DL-alaninate, DL-N-(2,6-dimethylphenyl)-N-(2'-methoxyacetyl)-alanine methyl ester, N-(2,6-dimethylphenyl)-N-chloroacetyl-D,L-2-amino-butyrolactone, DL-N-(2,6-dimethylphenyl)-N-(phenylacetyl)alanine methyl ester, 5-methyl-5-vinyl-3-(3,5-dichlorophenyl)2,4-dioxo-1,3-oxazolidine, 3-[3,5-dichlorophenyl(5-methyl-5-methoxymethyl]-1,3-oxazolidine-2,4-dione, 3-(3,5-dichlorophenyl)-1-isopropylcarbamoylhydantoin, N-(3,5-dichlorophenyl)-1, 2-dimethylcyclopropane-1,2-dicarboximide, 2-cyano-[N-(ethylaminocarbonyl)-2-methoximino]acetamide, 1-[2-(2,4-dichloro-phenyl)pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis(4-fluorophenyl)methylsilyl) methyl)-1H-1,2,4-triazole.

SYNTHESIS EXAMPLES

With due modification of the starting compounds, the protocols shown in the synthesis examples below were used for obtaining further compounds I. The resulting compounds, together with physical data, are listed in the Table which follows.

Example 1

Synthesis of (5,6-dihydro-[1,4,2]dioxazin-3-yl)-(2-orthotolyloxymethyl)phenylmethanone O-methyl oxime

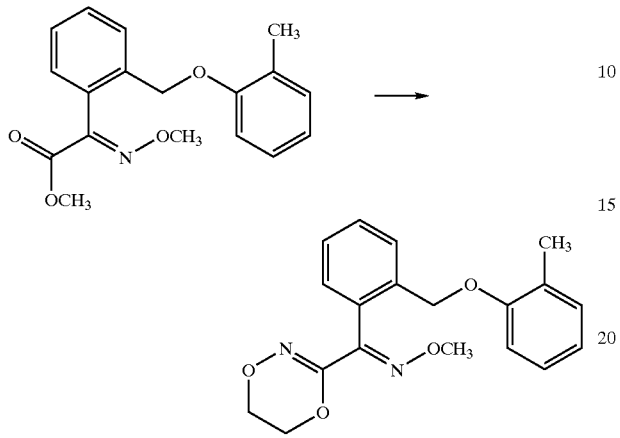

A solution of 62.7 g of hydroxylammonium chloride in 570 ml of anhydrous methanol and 93,9 g of methyl (E)-methoximino[α-(ortho-toloyloxy)ortho-tolyl]acetate [cf.: EP-A 253 213] were added to a solution of 59.4 g of potassium hydroxide (85%) in 270 ml of anhydrous methanol, and the mixture was refluxed for 4 hours. 141 g of 1,2-dibromoethane and 82.8 g of potassium carbonate were then added, and the mixture was stirred under reflux for a further 14 hours. The reaction mixture was then freed from the solvent, and the residue was taken up in ethyl acetate, washed with water and dried. Distillative removal of the solvent and chromatography over silica gel (cyclohexane/ethyl acetate mixture[1:1] gave 43.7 g of the product as a colorless amorphous powder of m.p. 104–106° C.

Example 2

Synthesis of (ortho-chloromethylphenyl) (5,6-dihydro-[1,4,2]dioxazin-3-yl)methanone O-methyl oxime

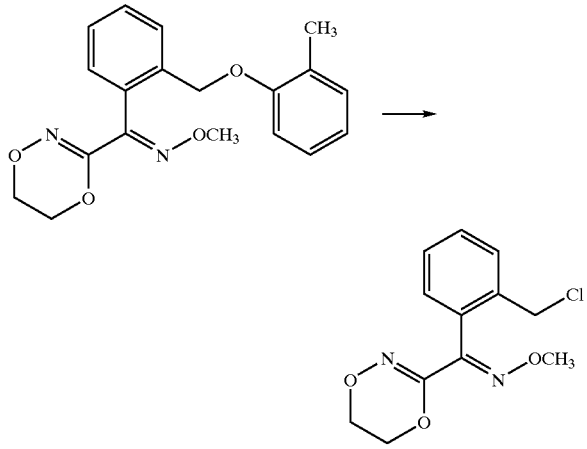

3.66 g of acetyl chloride were added dropwise to a suspension of 5.2 g of aluminum trichloride in 50 ml of anhydrous dichloromethane. A solution of 5.3 g of the oxime from Example 1 in 20 ml of anhydrous dichloromethane was subsequently added dropwise, and the mixture was stirred at 20–25 ° C. for three hours. The reaction solution was diluted with 100 ml of dichloromethane and then poured into ice-water. The phases were separated and the organic phase was washed with water, dried and freed from the solvent. Chromatography over silica gel (cyclohexane/ethyl acetate mixture [1:1]) gave 3.14 g of the title compound as light-beige crystals of m.p. 93–96° C.

Example 3

Synthesis of (ortho-[1-{4-chlorophenyl}-pyrazol-3-yl-oxymethyl]- phenyl)(5,6-dihydro-[1,4,2]dioxazin-3-yl)methanone O-methyl oxime

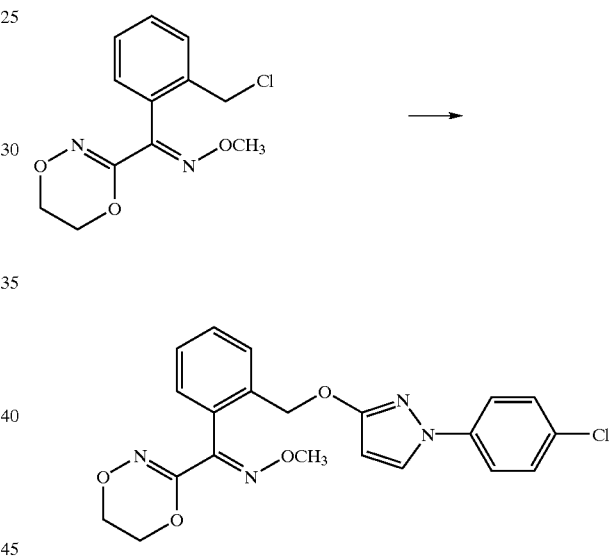

A solution of 0.97 g of 1-(para-chlorophenyl)-3-hydroxypyrazole in 20 ml of anhydrous dimethylformamide (DMF) was admixed with 0.13 g of sodium hydride and then stirred at 20–25 ° C. for approximately one hour. 1.34 g of the oxime from Example 2 were then added and the mixture was stirred at 60° C. for approximately three hours and then at 20–25° C. for approximately 14 hours. 300 ml of water were added and the mixture was then extracted with methyl tert-butyl ether (MTBE). The combined organic phases were washed with water and dried, and the solvent was then removed. The residue was chromatographed over silica gel (cyclohexane/ethyl acetate mixture [1:1]), giving 1.15 g of the title compound as a light-beige amorphous powder of m.p. 56–59° C.

IR [cm-1] : 1546, 1502, 1480, 1464, 1358, 1093, 1054, 998, 935, 906.

TABLE I

[Structure showing phenyl with oxazine-methoxime group and CH2-O-heterocycle with R2, R3, Y substituents]

| No. | Y | R² | R³ | phys. data (m.p. [° C.]; IR [cm⁻¹]) |
|---|---|---|---|---|
| I-1 | CH | H | 4-Cl—C₆H₄ | m.p.: 56–59; see Ex. 3 |
| I-2 | C—CH₃ | H | 2,4-Cl₂—C₆H₃ | m.p.: 122–123; IR: 1594, 1504, 1458, 1359, 1195, 1047, 998, 935, 906, 813 |
| I-3 | CH | H | 4-CH₃—C₆H₄ | m.p.: 128–129; IR: 1542, 1480, 1360, 1119, 1074, 1039, 995, 980, 907, 825 |
| I-4 | CH | H | 4-OCH₃—C₆H₄ | m.p.: 109–111; IR: 1539, 1515, 1480, 1248, 1072, 1036, 1023, 996, 910, 835 |
| I-5 | CH | H | 2,4-Cl₂—C₆H₃ | m.p.: 114–116; IR: 1544, 1473, 1453, 1352, 1056, 1041, 1028, 999, 906, 752 |
| I-6 | CH | CF₃ | 4-Cl—C₆H₄ | m.p.: 133–135; IR: 1508, 1490, 1149, 1134, 1092, 1055, 1042, 997, 985, 905 |
| I-7 | N | H | 4-Cl—C₆H₄ | IR: 1580, 1544, 1500, 1480, 1462, 1369, 1328, 1093, 1044, 998, 981, 972, 905, 831, 746 |
| I-8 | N | H | 2,4-Cl₂—C₆H₃ | IR: 1579, 1544, 1491, 1477, 1460, 1369, 1329, 1108, 1092, 1054, 1043, 998, 971, 905, 811 |
| I-9 | N | H | 4-F—C₆H₄ | IR: 1574, 1547, 1512, 1479, 1334, 1239, 1217, 1195, 1092, 1050, 1041, 997, 974, 906, 835 |
| I-10 | CH | H | 5-Cl-pyridin-2-yl | IR [cm⁻¹]: 1587, 1548, 1484, 1466, 1421, 1395, 1368, 1334, 1113, 1093, 1045, 998, 937, 905, 752 |
| I-11 | N | H | 5-Cl-pyridin-2-yl | m.p.: 173–175 |
| I-12 | C—Cl | Cl | CH₃ | m.p.: 146—149 |
| I-13 | CH | CF₃ | CH₃ | IR: 1566, 1493, 1463, 1366, 1275, 1191, 1149, 1127, 1093, 1081, 1055, 1042, 1016, 999, 907 |
| I-14 | C—Cl | CF₃ | CH₃ | m.p.: 94—96 |
| I-15 | CH | H | 2,4-(OCH₃)₂—C₆H₃—CH₂ | m.p.: 133–135; IR: 1508, 1490, 1149, 1134, 1092, 1055, 1042, 997, 985, 905 |

Examples of the Action Against Harmful Fungi

The fungicidal action of the compounds of the formula I was demonstrated by the following experiments:

The active compounds, separately or together, were formulated as a 10% emulsion in a mixture of 70% by weight of cyclohexanone, 20% by weight of Nekanil® LN (Lutensol® AP6, wetting agent having emulsifying and dispersant action based on ethoxylated alkylphenols) and 10% by weight of Wettol® EM (nonionic emulsifier based on ethoxylated castor oil) and diluted with water to the desired concentration.

The substances known from EP-A 757 042 (No. 20 of Table 2; Compound A), and from WO-A 95/04728 (No. 58 of Table 1; Compound B) served as comparative active compounds:

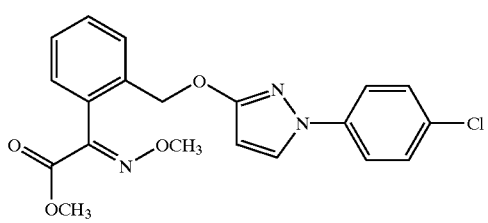

A

-continued

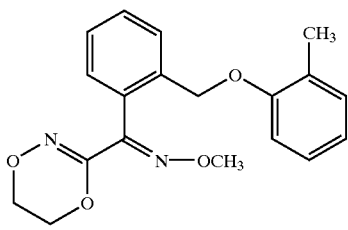

B

Use Example 1

Curative Action Against *Puccinia recondita* on Wheat (Wheat Leaf Rust)

Leaves of potted wheat seedlings of the variety "Kanzler" were dusted with spores of the wheat leaf rust (Puccinia recondita). Thereafter, the pots were kept in a chamber of high atmospheric humidity (90 to 95%) and 20 to 22° C. for 24 hours. During this time, the spores germinated and the germ tubes penetrated into the leaf tissue. The next day, the infected plants were sprayed to run-off point with an aqueous active compound formulation which had been made up from a stock solution consisting of 10% of active compound, 63% of cyclohexanone and 27% of emulsifier. After the spray coating had dried on, the test plants were cultivated in a greenhouse at 20–22° C. and 65–70% relative atmospheric humidity for 7 days. Thereafter, the extent of the rust fungus development on the leaves was determined.

In this test, the plants which had been treated with 16 ppm of compounds I-1, I-2, I-4 and I-10 showed no infection, whereas the plants which had been treated with 16 ppm of the comparative compounds A and B were infected to 60% and 90%, respectively, and untreated plants were infected to 100%.

Use Example 2

Action Against *Botrytis cinerea* on Bell Pepper Leaves

Bell pepper seedlings of the variety "Neusiedler Ideal Elite" were, after 4 to 5 leaves were well developed, sprayed to run-off point with an aqueous active compound formulation which had been made up from a stock solution consisting of 10% of active compound, 63% of cyclohexanone and 27% of emulsifier. The next day, the treated plants were inoculated with a spore suspension of Botrytis cinerea which contained $1.7 \times 10^6$ spores/ml in an aqueous 2% strength biomalt solution. The test plants were subsequently placed in a climatized chamber at 22–24° C. and high atmospheric humidity. After 5 days, the extent of the fungal infection on the leaves could be determined visually in %.

In this test, the plants that had been treated with 250 ppm of the compound I-1 showed an infection of 3%, whereas the plants which had been treated with 250 ppm of the comparative active compound A were infected to 40%, and the untreated plants were infected to 80%.

Use Example 3

Action Against *Pyricularia oryzae* (Protective)

Leaves of potted rice seedlings of the variety "Tai-Nong 67" were sprayed to run-off point with an aqueous active compound formulation which had been made up from a stock solution of 10% of active compound, 63% of cyclohexanone and 27% of emulsifier. The next day, the plants were inoculated with an aqueous spore suspension of Pyricularia oryzae. The test plants were subsequently kept in climatized chambers at 22–24° C. and 95–99% relative atmospheric humidity for 6 days. Thereafter, the extent of the development of the disease on the leaves was determined visually.

In this test, the plants which had been treated with 16 ppm of the compound I-1, I-2 and I-10 showed an infection of 10%, whereas the plants which had been treated with 16 ppm of the comparative active compound B were infected to 40%, and untreated plants were infected to 90%.

Use Example 4

Action Against Action Against [sic] *Phytophthora infestans* on Tomatoes

Leaves of potted plants of the variety "Große Fleischtomate St. Pierre" were sprayed to run-off point with an aqueous suspension which had been made up from a stock solution of 10% of active compound, 63% of cyclohexanone and 27% of emulsifier. The next day, the leaves were infected with a cold aqueous zoospore suspension of Phytophthora infestans having a density of $0.25 \times 10^6$ spores/ml. The plants were then placed in a water vapor-saturated chamber at 18–20° C. After 6 days, the late blight on the untreated but infected control plants had developed to such a degree that the infection could be determined visually in %.

In this test, the plants which had been treated with 250 ppm of the compounds I-4, I-10, I-12 and I-14 showed an infection of at most 5%, whereas the untreated plants were infected to 90%.

Examples of Action Against Animal Pests

The action of the compounds of the formula I against animal pests was demonstrated by the following experiments:

The active compounds were formulated a. as a 0.1% strength solution in acetone or b. as a 10% strength emulsion in a mixture of 70% by weight of cyclohexanone, 20% by weight of Nekanil® LN (Lutensol® AP6, wetting agent having emulsifying and dispersant action based on ethoxylated alkylphenols) and 10% by weight of Wettol® EM (nonionic emulsifier based on ethoxylated castor oil)

and diluted in the case of a. with acetone and in the case of b. with water to be the desired concentration.

After the experiments had ended, in each case the lowest concentration was determined in which the compounds still caused an 80 to 100% inhibition or mortality in comparison with untreated control experiments (limit or minimal concentration).

We claim:
1. A compound of formula I

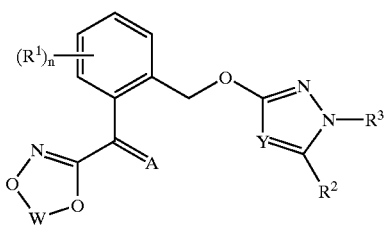

where the substituents and the index have the following meanings:

Y is N or CR$^a$, n is 0, 1, 2, 3 or 4, where the substituents R$^1$ may be different if n is greater than 1;

R$^1$ is nitro, cyano, halogen, C$_1$–C$_6$-alkyl or, if n is greater than 1, additionally a bridge which is attached to two adjacent ring atoms and which contains three to four members selected from the group consisting of: 3 or 4 carbon atoms, 2 to 3 carbon atoms and 1 or 2 nitrogen, oxygen and/or sulfur atoms, where this bridge, together with the ring to which is is attached, may form a partially unsaturated or aromatic ring and where furthermore the carbon atoms or the bridge may be partially or fully substituted by halogen atoms or methyl groups;

R$^2$ is hydrogen, nitro, cyano, halogen, C$_1$–C$_4$-alkyl, C$_1$–C$_4$-haloalkyl, C$_1$–C$_4$-alkoxy, C$_1$–C$_4$-alkylthio or C$_1$–C$_4$-alkoxycarbonyl;

R$^3$ is C$_1$–C$_6$-alkyl which is unsubstituted or partially or fully halogenated or may carry one to three groups R$^b$, C$_3$–C$_6$-cycloalkyl, aryl or hetaryl, where the cyclic systems may be partially or fully halogenated or may carry one to three groups R$^c$;

A is =N—OR$^4$, =CH—OR$^4$, =CH—SR$^4$ or =CH—R$^5$,

R$^4$ is C$_1$–C$_4$-alkyl or C$_1$–C$_4$-haloalkyl,

R$^5$ is halogen or a group R$^4$,

W is C$_1$–C$_3$-alkylene which is unsubstituted or substituted by one or two groups R$^e$, R$^a$ is hydrogen, halogen or C$_1$–C$_4$-alkyl;

R$^b$ is halogen, cyano, nitro, hydroxyl, C$_1$–C$_6$-alkyl, C$_1$–C$_6$-haloalkyl, C$_1$–C$_6$-alkylcarbonyl, C$_3$–C$_6$-cycloalkyl, C$_1$–C$_6$-alkoxy, C$_1$–C$_6$-haloalkoxy, C$_1$–C$_6$-alkoxycarbonyl, C$_1$–C$_6$-alkylthio, C$_1$–C$_6$-alkylamino, di-C$_1$–C$_6$-alkylamino, C$_2$–C$_6$-alkenyl, C$_2$–C$_6$-alkenyloxy, C$_3$–C$_6$-alkynyloxy and C$_1$–C$_4$-alkylenedioxy, which may be halogenated;

R$^c$ is halogen, cyano, nitro, hydroxyl, mercapto, amino, carboxyl, aminocarbonyl, aminothiocarbonyl, alkyl, haloalkyl, alkenyl, alkenyloxy, alkynyloxy, alkoxy, haloalkoxy, alkylthio, alkylamino, dialkylamino, formyl, alkylcarbonyl, alkylsulfonyl, alkylsulfoxyl, alkoxycarbonyl, alkylcarbonyloxy, alkylaminocarbonyl, dialkylaminocarbonyl, alkylaminothiocarbonyl, dialkylaminothiocarbonyl, where the alkyl groups in these radicals contain 1 to 6 carbon atoms and the abovementioned alkenyl or alkynyl groups in these radicals contain 2 to 8 carbon atoms, or is C(=NOR$^d$)-Γ$_1$-R$^d$, where R$^d$ is hydrogen or C$_1$–C$_6$-alkyl, Γ is oxygen, sulfur or NR$^d$, and l is 0 or 1, and/or is one to three of the following radicals: cycloalkyl, cycloalkoxy, heterocyclyl, heterocyclyloxy, where the cyclic systems contain 3 to 10 ring members; aryl, aryloxy, arylthio, aryl-C$_1$–C$_6$-alkoxy, aryl-C$_1$–C$_6$-alkyl, hetaryl, hetaryloxy, hetarylthio, where the aryl radicals contain 6 to 10 ring members and the hetaryl radicals 5 or 6 ring members and where the cyclic systems may be partially or fully halogenated or may be substituted by one to three groups R$^b$;

R$^e$ is halogen, cyano, C$_1$–C$_4$-alkyl, C$_1$–C$_4$-haloalkyl, C$_2$–C$_4$-alkenyl, C$_2$–C$_4$-haloalkenyl, C$_2$–C$_4$-alkynyl or C$_2$–C$_4$-haloalkynyl, C$_1$–C$_4$-alkoxy, C$_1$–C$_4$-haloalkoxy, C$_2$–C$_4$-alkenyloxy, C$_2$–C$_4$-haloalkenyloxy, C$_2$–C$_4$-alkynyloxy or C$_2$–C$_4$-haloalkynyloxy, C$_1$–C$_4$-alkylcarbonyloxy.

2. A compound of formula I',

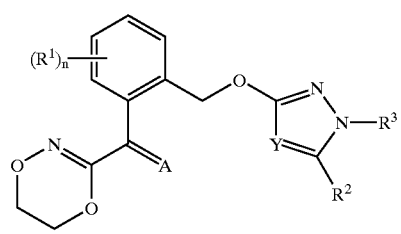

in which

R$^1$ is 6-Cl or 6-CH$_3$;

n is 0 or 1;

A is =N—OCH$_3$, =CH—OCH$_3$ or =CH—CH$_3$ and

Y, R$^2$ and R$^3$ are as defined in claim 1.

3. A process for preparing the compound of formula I defined in claim I, which comprises reacting a benzyl halide of formula II,

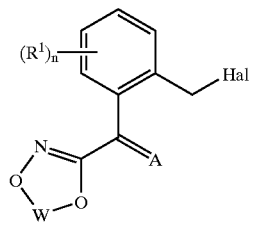

in which Hal is a halogen atom with a compound of formula III,

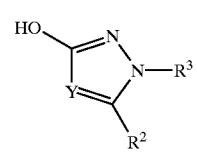

in the presence of a base.

4. A process for preparing the compound of formula I defined in claim 1, which comprises reacting a phenylacetic acid compound of formula IVa,

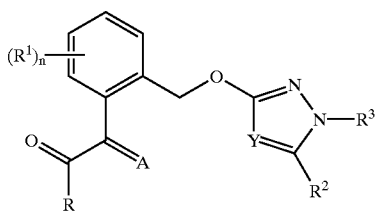

in which R is halogen, $C_1$–$C_6$-alkylcarbonyloxy, OH, $C_1$–$C_4$-alkoxy, phenoxy or azido, optionally in the presence of a base and/or a coupling reagent, with hydroxylamine or an acid addition thereof to give a hydroxamic acid of formula IVb,

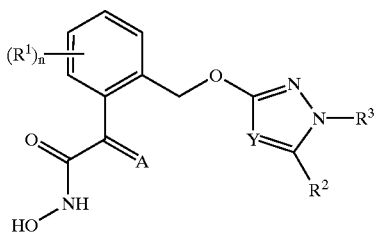

and reacting IVb with a compound of formula Va

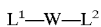

in which $L^1$ and $L^2$ are each a nucleophilically replaceable group, optionally in the presence of a base or of a dehydrating agent.

5. An intermediate of formula IVb

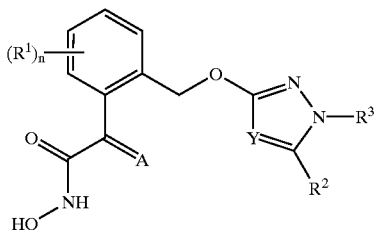

wherein

Y is N or $CR^a$, n is 0, 1, 2, 3 or 4, where the substituents $R^1$ may be different if n is greater than 1;

$R^1$ is nitro, cyano, halogen, $C_1$–$C_6$-alkyl or, if n is greater than 1, additionally a bridge which is attached to two adjacent ring atoms and which contains three to four members selected from the group consisting of: 3 or 4 carbon atoms, 2 to 3 carbon atoms and 1 or 2 nitrogen, oxygen and/or sulfur atoms, where this bridge, together with the ring to which is is attached, may form a partially unsaturated or aromatic ring and where furthermore the carbon atoms or the bridge may be partially or fully substituted by halogen atoms or methyl groups;

$R^2$ is hydrogen, nitro, cyano, halogen, $C_1$–$C_4$-alkyl, $C_1$–$C_4$-haloalkyl, $C_1$–$C_4$-alkoxy, $C_1$–$C_4$-alkylthio or $C_1$–$C_4$-alkoxycarbonyl;

$R^3$ is $C_1$–$C_6$-alkyl which is unsubstituted or partially or fully halogenated or may carry one to three groups $R^b$, $C_3$–$C_6$-cycloalkyl, aryl or hetaryl, where the cyclic systems may be partially or fully halogenated or may carry one to three groups $R^c$;

A is =N—$OR^4$, =CH—$OR^4$, =CH—$SR^4$ or =CH—$R^5$, $R^4$ is $C_1$–$C_4$-alkyl or $C_1$–$C_4$-haloalkyl, $R^5$ is halogen or a group $R^4$, $R^a$ is hydrogen, halogen or $C_1$–$C_4$-alkyl;

$R^b$ is halogen, cyano, nitro, hydroxyl, $C_1$–$C_6$-alkyl, $C_1$–$C_6$-haloalkyl, $C_1$–$C_6$-alkylcarbonyl, $C_3$–$C_6$-cycloalkyl, $C_1$–$C_6$-alkoxy, $C_f$–$C_6$-haloalkoxy, $C_f$–$C_6$-alkoxycarbonyl, $C_f$–$C_6$-alkylthio, $C_f$–$C_6$-alkylamino, di-$C_f$–$C_6$-alkylamino, $C_2$–$C_6$-alkenyl, $C_2$–$C_6$-alkenyloxy, $C_3$–$C_6$-alkynyloxy and $C_1$–$C_4$-alkylenedioxy, which may be halogenated;

$R^c$ is halogen, cyano, nitro, hydroxyl, mercapto, amino, carboxyl, aminocarbonyl, aminothiocarbonyl, alkyl, haloalkyl, alkenyl, alkenyloxy, alkynyloxy, alkoxy, haloalkoxy, alkylthio, alkylamino, dialkylamino, formyl, alkylcarbonyl, alkylsulfonyl, alkylsulfoxyl, alkoxycarbonyl, alkylcarbonyloxy, alkylaminocarbonyl, dialkylaminocarbonyl, alkylaminothiocarbonyl, dialkylaminothiocarbonyl, where the alkyl groups in these radicals contain 1 to 6 carbon atoms and the abovementioned alkenyl or alkynyl groups in these radicals contain 2 to 8 carbon atoms, or is C(=$NOR^d$)-$\Gamma_1$-$R^d$, where $R^d$ is hydrogen or $C_1$–$C_6$-alkyl, $\Gamma$ is oxygen, sulfur or $NR^d$, and 1 is 0 or 1, and/or is one to three of the following radicals: cycloalkyl, cycloalkoxy, heterocyclyl, heterocyclyloxy, where the cyclic systems contain 3 to 10 ring members; aryl, aryloxy, arylthio, aryl-$C_1$–$C_6$-alkoxy, aryl-$C_1$–$C_6$-alkyl, hetaryl, hetaryloxy, hetarylthio, where the aryl radicals contain 6 to 10 ring members and the hetaryl radicals 5 or 6 ring members and where the cyclic systems may be partially or fully halogenated or may be substituted by one to three groups $R^b$.

6. A composition suitable for controlling animal pests or harmful fungi, comprising a solid or liquid carrier and the compound of formula I defined in claim 1.

7. A method for preparing the composition defined in claim 6, which comprises admixing an effective amount of the compound of formula I with at least one solid or liquid carrier.

8. A method for controlling harmful fungi, which comprises treating the fungi or materials, plants, soil or seed to be protected against fungal attack with an effective amount of the compound of formula I defined in claim 1.

9. A method for controlling animal pests, which comprises treating the animal pests or materials, plants, soil or seed to be protected against them with an effective amount of the compound of formula I defined in claim 1.

* * * * *

UNITED STATES PATENT AND TRADEMARK OFFICE
CERTIFICATE OF CORRECTION

PATENT NO.     : 6,451,790 B1
DATED          : September 17, 2002
INVENTOR(S)    : Gewehr et al.

It is certified that error appears in the above-identified patent and that said Letters Patent is hereby corrected as shown below:

Title page,
Item [22], "Jan. 4, 2001" should be -- Jan. 4, 2000 --.

Column 46,
Lines 16-20, each occurrence of "$C_l$-$C_6$-" should be -- $C_1$-$C_6$- --.

Signed and Sealed this

Ninth Day of September, 2003

JAMES E. ROGAN
*Director of the United States Patent and Trademark Office*